United States Patent
Chambers et al.

[11] Patent Number: 5,925,638
[45] Date of Patent: Jul. 20, 1999

[54] SUBSTITUTED 1-INDOLYLPROPYL-4-BENZYLPIPERAZINE DERIVATIVES

[75] Inventors: Mark Stuart Chambers, Puckeridge; Sarah Christine Hobbs, Great Dunmow; Leslie Joseph Street, Harlow, all of United Kingdom

[73] Assignee: Merck Sharp & Dohme Ltd., Hoddesdon, United Kingdom

[21] Appl. No.: 09/068,072

[22] PCT Filed: Nov. 4, 1996

[86] PCT No.: PCT/GB96/02682

§ 371 Date: Apr. 28, 1998

§ 102(e) Date: Apr. 28, 1998

[87] PCT Pub. No.: WO97/17338

PCT Pub. Date: May 15, 1997

[30] Foreign Application Priority Data

Nov. 10, 1995 [GB] United Kingdom ............. 9523065

[51] Int. Cl.⁶ .............. A61K 31/495; C07D 403/14
[52] U.S. Cl. .............. 514/253; 544/366; 544/367; 544/369; 544/370
[58] Field of Search .............. 544/366, 369, 544/367, 370; 514/253

[56] References Cited

U.S. PATENT DOCUMENTS

| | | | |
|---|---|---|---|
| 5,614,524 | 3/1997 | Matassa et al. | 514/253 |
| 5,807,857 | 9/1998 | Pineiro et al. | 514/253 |
| 5,808,064 | 9/1998 | Chen et al. | 544/132 |

FOREIGN PATENT DOCUMENTS

| | | |
|---|---|---|
| 94/02477 | 2/1994 | WIPO . |
| 95/32196 | 11/1995 | WIPO . |
| 96/16056 | 5/1996 | WIPO . |
| 98/06725 | 2/1998 | WIPO . |

*Primary Examiner*—Mukund J. Shah
*Assistant Examiner*—Ann M. Kessinger
*Attorney, Agent, or Firm*—Philippe L. Durette; Melvin Winokur

[57] ABSTRACT

A class of 1-[3-(1H-indol-3-yl)propyl]-4-benzylpiperazine derivatives of formula I, substituted at the 5-position of the indole nucleus by a 1,2,4-triazol-4-yl moiety, and on the methylene linkage of the benzyl moiety by a range of substituted alkyl groups, are selective agonists of 5-HT$_1$-like receptors, being potent agonists of the human 5-HT$_{1D\alpha}$ receptor subtype whilst possessing at least a 10-fold selective affinity for the 5-HT$_{1D\alpha}$ receptor subtype relative to the 5-HT$_{1D\beta}$ subtype; they are therefore useful in the treatment and/or prevention of clinical conditions, in particular migraine and associated disorders, for which a subtype-selective agonist of 5-HT$_{1D}$ receptors is indicated, whilst eliciting fewer side-effects, notably adverse cardiovascular events, than those associated with non-subtype-selective 5-HT$_{1D}$ receptor agonists.

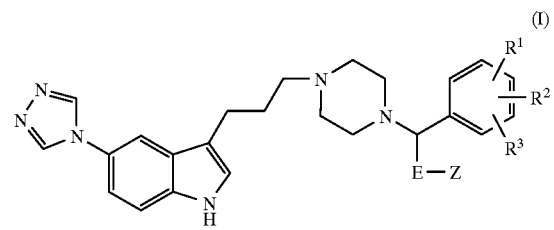

11 Claims, No Drawings

SUBSTITUTED 1-INDOLYLPROPYL-4-BENZYLPIPERAZINE DERIVATIVES

The present invention relates to a class of substituted piperazine derivatives which act on 5-hydroxytryptamine (5-HT) receptors, being selective agonists of so-called "5-HT$_1$-like" receptors. They are therefore useful in the treatment of clinical conditions for which a selective agonist of these receptors is indicated.

It has been known for some time that 5-HT$_1$-like receptor agonists which exhibit selective vasoconstrictor activity are of use in the treatment of migraine (see, for example, A. Doenicke et al., *The Lancet,* 1988, Vol. 1, 1309–11; and W. Feniuk and P. P. A. Humphrey, *Drug Development Research,* 1992, 26, 235–240).

The human 5-HT$_1$-like or 5-HT$_{1D}$ receptor has recently been shown by molecular cloning techniques to exist in two distinct subtypes. These subtypes have been termed 5-HT$_{1D\alpha}$ (or 5-HT$_{1D-1}$) and 5-HT$_{1D\beta}$ (or 5-HT$_{1D-2}$), and their amino acid sequences are disclosed and claimed in WO-A-91/17174.

The 5-HT$_{1D\alpha}$ receptor subtype in humans is believed to reside on sensory terminals in the dura mater. Stimulation of the 5-HT$_{1D\alpha}$ subtype inhibits the release of inflammatory neuropeptides which are thought to contribute to the headache pain of migraine. The human 5-HT$_{1D\beta}$ receptor subtype, meanwhile, is located predominantly on the blood vessels and in the brain, and hence may play a part in mediating constriction of cerebral and coronary arteries, as well as CNS effects.

Administration of the prototypical 5-HT$_{1D}$ agonist sumatriptan (GR43175) to humans is known to give rise at therapeutic doses to certain adverse cardiovascular events (see, for example, F. Willett et al., *Br. Med. J.,* 1992, 304, 1415; J. P. Ottervanger et al., *The Lancet,* 1993, 341, 861–2; and D. N. Bateman, *The Lancet,* 1993, 341, 221–4). Since sumatriptan barely discriminates between the human 5-HT$_{1D\alpha}$ and 5-HT$_{1D\beta}$ receptor subtypes (cf. WO-A-91/17174, Table 1), and since it is the blood vessels with which the 5-HT$_{1D\beta}$ subtype is most closely associated, it is believed that the cardiovascular side-effects observed with sumatriptan can be attributed to stimulation of the 5-HT$_{1D\beta}$ receptor subtype. It is accordingly considered (cf G. W. Rebeck et al., *Proc. Natl. Acad. Sci. USA,* 1994, 91, 3666–9) that compounds which can interact selectively with the 5-HT$_{1D\alpha}$ receptor subtype, whilst having a less pronounced action at the 5-HT$_{1D\beta}$ subtype, might be free from, or at any rate less prone to, the undesirable cardiovascular and other side-effects associated with non-subtype-selective 5-HT$_{1D}$ receptor agonists, whilst at the same time maintaining a beneficial level of anti-migraine activity.

The compounds of the present invention, being selective 5-HT$_1$-like receptor agonists, are accordingly of benefit in the treatment of migraine and associated conditions, e.g. cluster headache, chronic paroxysmal hemicrania, headache associated with vascular disorders, tension headache and paediatric migraine. In particular, the compounds according to this invention are potent agonists of the human 5-HT$_{1D\alpha}$ receptor subtype. Moreover, the compounds in accordance with this invention have been found to possess at least a 10-fold selective affinity for the 5-HT$_{1D\alpha}$ receptor subtype relative to the 5-HT$_{1D\beta}$ subtype, and they can therefore be expected to manifest fewer side-effects than those associated with non-subtype-selective 5-HT$_{1D}$ receptor agonists.

Several distinct classes of substituted five-membered heteroaromatic compounds are described in published European patent application 0497512, and published International patent applications 93/18029, 94/02477 and 94/03446. The compounds described therein are stated to be agonists of 5-HT$_1$-like receptors, and accordingly to be of particular use in the treatment of migraine and associated conditions. None of these publications, however, discloses nor even suggests the substituted piperazine derivatives provided by the present invention.

In EP-A-0548813 is described a series of alkoxypyridin-4-yl and alkoxypyrimidin-4-yl derivatives of indol-3-ylalkylpiperazines which are alleged to provide treatment of vascular or vascular-related headaches, including migraine. There is, however, no disclosure nor any suggestion in EP-A-0548813 of replacing the alkoxypyridine or alkoxypyrimidine substituent with a substituted benzyl moiety; nor is there any suggestion therein that the range of substituents specified at the 5-position of the indole moiety might be replaced by a 1,2,4-triazol-4-yl ring.

Moreover, nowhere in the prior art mentioned above is there any disclosure of a subtype-selective 5-HT$_{1D}$ receptor agonist having a 5-HT$_{1D\alpha}$ receptor binding affinity (IC$_{50}$) below 50 nM and at least a 10-fold selective affinity for the 5-HT$_{1D\alpha}$ receptor subtype relative to the 5-HT$_{1D\beta}$ subtype.

The compounds according to the present invention are subtype-selective 5-HT$_{1D}$ receptor agonists having a human 5-HT$_{1D\alpha}$ receptor binding affinity (IC$_{50}$) below 50 nM, typically below 10 nM and preferably below 1 nM; and at least a 10-fold selective affinity, typically at least a 50-fold selective affinity and preferably at least a 100-fold selective affinity, for the human 5-HT$_{1D\alpha}$ receptor subtype relative to the 5-HT$_{1D\beta}$ subtype. Moreover, the compounds in accordance with this invention possess interesting properties in terms of their efficacy and/or bioavailability.

The present invention provides a compound of formula I, or a salt or prodrug thereof:

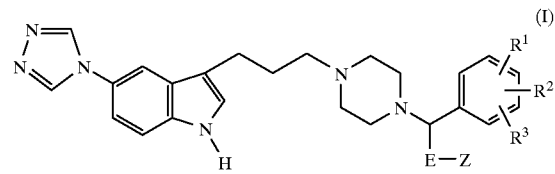

wherein

R$^1$ represents hydrogen, halogen, trifluoromethyl, C$_{1-6}$ alkoxy or a group of formula (a):

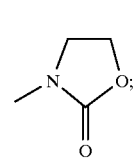

R$^2$ and R$^3$ independently represent hydrogen, halogen, trifluoromethyl or C$_{1-6}$ alkoxy;

E represents a straight or branched alkylene chain containing from 1 to 4 carbon atoms; and Z represents hydroxy, C$_{1-6}$ alkoxy, aryl(C$_{1-6}$)alkoxy, an imidazolyl or pyrrolidinyl group, or a group of formula (Za) or (Zb):

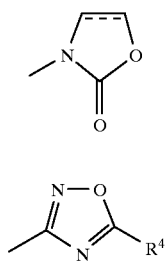

in which the broken line represents an optional chemical bond; and $R^4$ represents $C_{1-6}$ alkyl.

The compounds in accordance with the present invention are encompassed within the generic scope of co-pending International Patent Application No. PCT/GB95/01129, published as WO 95/32196 on Nov. 30, 1995. There is, however, no specific disclosure therein of compounds corresponding to those of formula I above wherein $R^1$, $R^2$, $R^3$, E and Z are as defined above.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$C_{1-6}$ alkoxy" are to be construed accordingly.

The term "aryl" as used herein includes phenyl and naphthyl.

A typical aryl($C_{1-6}$)alkoxy group is benzyloxy.

The term "halogen" as used herein includes fluorine, chlorine, bromine and iodine, especially fluorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in Design of Prodrugs, ed. H. Bundgaard, Elsevier, 1985.

The compounds according to the invention have at least one asymmetric centre, and they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In the compounds of formula I above, the moiety $R^1$ suitably represents hydrogen, fluoro, trifluoromethyl, methoxy or a group of formula (a) as defined above. Particular values of $R^1$ include hydrogen, fluoro and trifluoromethyl, especially hydrogen or fluoro.

Suitably, $R^2$ and $R^3$ independently represent hydrogen, fluoro, trifluoromethyl or methoxy, in particular hydrogen or fluoro. Suitably, one or both of $R^2$ and $R^3$ represents hydrogen.

Suitably, $R^4$ represents methyl.

The alkylene chain E in the compounds of formula I above may be, for example, methylene, ethylene, 1-methylethylene, propylene, 2-methylpropylene or butylene. Suitably, E represents a methylene or ethylene linkage.

Particular values for the substituent Z include hydroxy, methoxy, benzyloxy, imidazol-1-yl, pyrrolidin-1-yl, oxazol-2-on-3-yl, oxazolidin-2-on-3-yl and 5-methyl-1,2,4-oxadiazol-3-yl.

A particular sub-class of compounds according to the invention is represented by the compounds of formula II, and salts and prodrugs thereof:

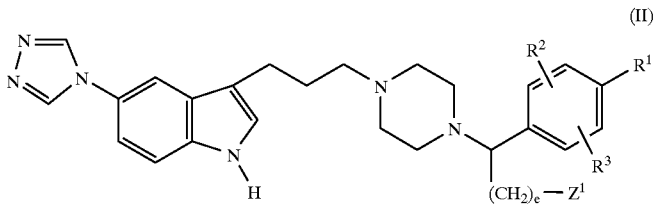

wherein $R^1$, $R^2$ and $R^3$ are as defined above;

e is 1 or 2; and $Z^1$ represents hydroxy, methoxy, benzyloxy, imidazol-1-yl, pyrrolidin-1-yl, oxazol-2-on-3-yl, oxazolidin-2-on-3-yl or 5-methyl-1,2,4-oxadiazol-3-yl.

Particular values of $R^1$ in relation to formula II above include hydrogen, fluoro and trifluoromethyl, especially hydrogen or fluoro.

In one embodiment of the compounds of formula II above, $R^2$ is hydrogen and $R^3$ is other than hydrogen.

In another embodiment of the compounds of formula II above, $R^2$ and $R^3$ are both hydrogen.

Specific compounds within the scope of the present invention include:

1-[3-(5-(1,2,4-triazol-4-yl)-1H-indol-3-yl)propyl]-4-[2-(oxazol-2-on-3-yl)-1-phenylethyl]piperazine;

1-[3-(5-(1,2,4-triazol-4-yl)-1H-indol-3-yl)propyl]-4-[2-(oxazolidin-2-on-3-yl)-1-phenylethyl]piperazine;

1-[3-(5-(1,2,4-triazol-4-yl)-1H-indol-3-yl)propyl]-4-[1-(4-fluorophenyl)-2-(oxazolidin-2-on-3-yl)ethyl]piperazine;

1-[3-(5-(1,2,4-triazol-4-yl)-1H-indol-3-yl)propyl]-4-(3-hydroxy-1-phenylpropyl)piperazine;

1-[3-(5-(1,2,4-triazol-4-yl)-1H-indol-3-yl)propyl]-4-[2-(imidazol-1-yl)-1-phenylethyl]piperazine;

1-[3-(5-(1,2,4-triazol-4-yl)-1H-indol-3-yl)propyl]-4-[1-(4-fluorophenyl)-2-hydroxyethyl]piperazine;

1-[3-(5-(1,2,4-triazol-4-yl)-1H-indol-3-yl)propyl]-4-[1-(4-fluorophenyl)-2-methoxyethyl]piperazine;
1-[3-(5-(1,2,4-triazol-4-yl)-1H-indol-3-yl)propyl]-4-[3-(5-methyl-1,2,4-oxadiazol-3-yl)-1-phenylpropyl]piperazine;
1-[3-(5-(1,2,4-triazol-4-yl)-1H-indol-3-yl)propyl]-4-[2-benzyloxy-1-(4-fluorophenyl)ethyl]piperazine;
1-[3-(5-(1,2,4-triazol-4-yl)-1H-indol-3-yl)propyl]-4-[1-(4-fluorophenyl)-3-methoxypropyl]piperazine;
1-[3-(5-(1,2,4-triazol-4-yl)-1H-indol-3-yl)propyl]-4-[1-(4-fluorophenyl)-2-(imidazol-1-yl)ethyl]piperazine;
1-[3-(5-(1,2,4-triazol-4-yl)-1H-indol-3-yl)propyl]-4-[1-phenyl-2-(pyrrolidin-1-yl)ethyl]piperazine;
1-[3-(5-(1,2,4-triazol-4-yl)-1H-indol-3-yl)propyl]-4-[1-(4-fluorophenyl)-3-hydroxypropyl]piperazine;
1-[3-(5-(1,2,4-triazol-4-yl)-1H-indol-3-yl)propyl]-4-[3-(imidazol-1-yl)-1-phenylpropyl]piperazine;

and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to the invention may be prepared by a process which comprises reacting the compound of formula III with a compound of formula IV:

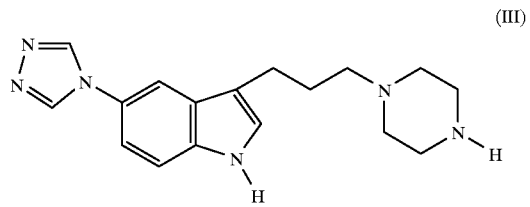

(III)

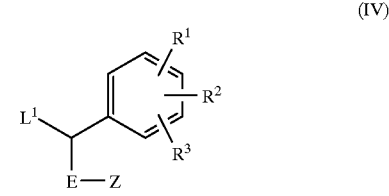

(IV)

wherein $R^1$, $R^2$, $R^3$, E and Z are as defined above, and $L^1$ represents a suitable leaving group.

The leaving group $L^1$ is suitably a halogen atom, e.g. chlorine or bromine, or an alkylsulphonyloxy or arylsulphonyloxy group, e.g. methanesulphonyloxy (mesyloxy) or p-toluenesulphonyloxy (tosyloxy).

The reaction between compounds III and IV is conveniently effected by stirring the reactants under basic conditions in a suitable solvent, for example triethylamine or potassium carbonate in N,N-dimethylformamide or isopropanol, typically in the presence of sodium iodide.

In another procedure, the compounds according to the invention may be prepared by a process which comprises reacting the compound of formula III as defined above with a compound of formula V:

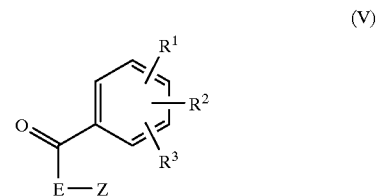

(V)

wherein $R^1$, $R^2$, $R^3$, E and Z are as defined above; in the presence of a reducing agent.

A suitable reducing agent for effecting this process is sodium cyanoborohydride, and the reaction is conveniently carried out in methanol, typically in the presence of acetic acid, at room temperature.

The compound of formula III above may be prepared by a process which comprises reacting the compound of formula VI:

(VI)

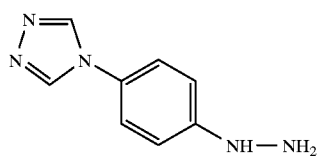

with a compound of formula VII, or a carbonyl-protected form thereof:

(VII)

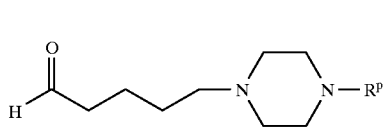

wherein $R^P$ represents an amino-protecting group; with subsequent removal of the amino-protecting group $R^P$.

The reaction between compounds VI and VII, which is an example of the well-known Fischer indole synthesis, is suitably carried out by heating the reagents together under mildly acidic conditions, e.g. 4% sulphuric acid at reflux.

Suitable carbonyl-protected forms of the compounds of formula VII include the dimethyl acetal derivatives.

The protecting group $R^P$ in the compounds of formula VII is suitably a carbamoyl moiety such as tert-butoxycarbonyl (BOC), which can conveniently be removed as necessary by treatment under mildly acidic conditions. Indeed, the acidic conditions of the Fischer indole synthesis reaction will generally suffice to remove the BOC group.

The Fischer reaction between compounds VI and VII may be carried out in a single step, or may proceed via an initial non-cyclising step at a lower temperature to give an intermediate of formula VIII:

(VIII)

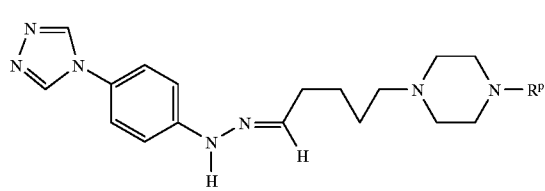

wherein $R^P$ is as defined above; followed by cyclisation using a suitable reagent, e.g. a polyphosphate ester.

The intermediates of formula VII, or carbonyl-protected forms thereof, may be prepared by reacting a compound of formula IX, or a carbonyl-protected form thereof, with a compound of formula X:

(IX)

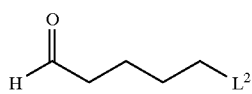

(X)

wherein $R^P$ is as defined above, and $L^2$ represents a suitable leaving group.

The leaving group $L^2$ is suitably a halogen atom, e.g. chlorine or bromine.

Where $L^2$ represents a halogen atom, the reaction between compounds IX and X is conveniently effected by stirring the reactants under basic conditions in a suitable solvent, for example potassium carbonate in N,N-dimethylformamide, or triethylamine in tetrahydrofuran or acetonitrile.

The compounds according to the invention may alternatively be prepared by a process which comprises reacting the compound of formula VI as defined above with a compound of formula XI, or a carbonyl-protected form thereof:

(XI)

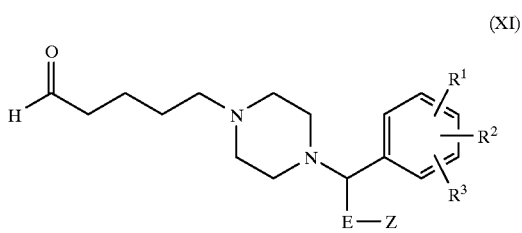

wherein $R^1$, $R^2$, $R^3$, E and Z are as defined above; under conditions analogous to those described above for the reaction between compounds VI and VII.

As for the compounds of formula VII, suitable carbonyl-protected forms of the compounds of formula XI include the dimethyl acetal derivatives.

As with that between compounds VI and VII, the Fischer reaction between compounds VI and XI may be carried out in a single step, or may proceed via an initial non-cyclising step at a lower temperature to give an intermediate of formula XII:

(XII)

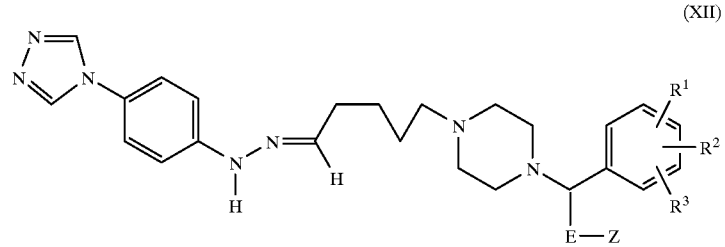

wherein $R^1$, $R^2$, $R^3$, E and Z are as defined above; followed by cyclisation using a suitable reagent, e.g. a polyphosphate ester.

The intermediates of formula XI, or carbonyl-protected forms thereof, may be prepared by reacting a compound of formula IX as defined above, or a carbonyl-protected form thereof, with a compound of formula XIII:

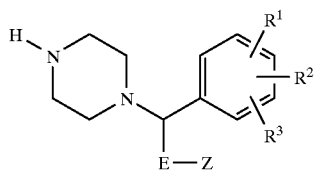

(XIII)

wherein $R^1$, $R^2$, $R^3$, E and Z are as defined above; under conditions analogous to those described above for the reaction between compounds IX and X.

In an alternative procedure, the compounds of formula III above may be prepared by a process which comprises reacting a compound of formula X as defined above with a compound of formula XIV:

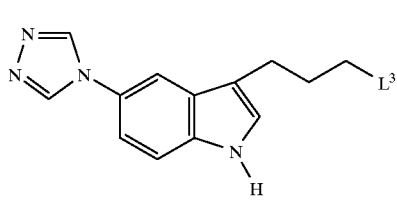

(XIV)

wherein $L^3$ represents a suitable leaving group; followed by removal of the amino-protecting group $R^p$.

Similarly, the compounds of formula I as defined above may be prepared by a process which comprises reacting a compound of formula XIII as defined above with a compound of formula XIV as defined above.

The leaving group $L^3$ is suitably an alkylsulphonyloxy or arylsulphonyloxy group, e.g. methanesulphonyloxy (mesyloxy) or p-toluenesulphonyloxy (tosyloxy).

Where $L^3$ represents an alkylsulphonyloxy or arylsulphonyloxy group, the reaction between compound XIV and compound X or XIII is conveniently carried out in a suitable solvent such as 1,2-dimethoxyethane or isopropyl alcohol, typically in the presence of a base such as sodium carbonate or potassium carbonate, optionally with the addition of sodium iodide.

In one representative approach, the compounds of formula XIV wherein $L^3$ represents a mesyloxy or tosyloxy group may be prepared by the sequence of steps illustrated in the following reaction scheme (cf. Larock and Yum, *J. Am. Chem. Soc.*, 1991, 113, 6689):

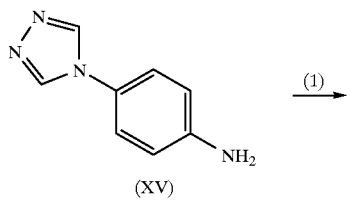

(XV)

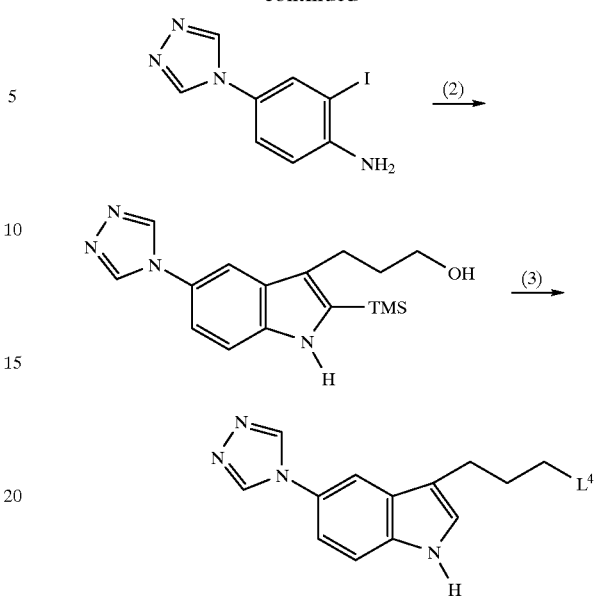

wherein $L^4$ represents mesyloxy or tosyloxy, and TMS is an abbreviation for trimethylsilyl.

In Step 1 of the reaction scheme, the aniline derivative XV is treated with iodine monochloride, advantageously in methanol in the presence of a base such as calcium carbonate, in order to introduce an iodine atom ortho to the amine moiety. Step 2 involves a palladium-mediated coupling reaction with the protected acetylene derivative TMS—C≡C—$(CH_2)_3$—OH, typically using palladium acetate and triphenylphosphine in the presence of lithium chloride and sodium carbonate, suitably in N,N-dimethylformamide at an elevated temperature. This is followed in Step 3 by removal of the TMS moiety, ideally in refluxing methanolic hydrochloric acid; followed in turn by mesylation or tosylation, suitably by using mesyl chloride or tosyl chloride respectively in pyridine.

In another representative approach, the compounds of formula XIV wherein $L^3$ represents a mesyloxy or tosyloxy group may be prepared by reacting 3,4-dihydro-2H-pyran with the compound of formula VI as defined above or a salt thereof, under a variant of the Fischer reaction conditions as described above for the reaction between compounds VI and VII; followed by mesylation or tosylation of the 3-hydroxypropyl-indole derivative thereby obtained, typically by treatment with mesyl chloride or tosyl chloride under standard conditions.

The Fischer reaction with 3,4-dihydro-2H-pyran is suitably brought about by heating the hydrazine derivative VI or an acid addition salt thereof, typically the hydrochloride salt, in an inert solvent such as dioxan, advantageously in the presence of a mineral acid such as hydrochloric acid or a Lewis acid such as zinc chloride, at the reflux temperature of the solvent.

In a further procedure, the compounds of formula III above may be prepared by a process which comprises reducing a compound of formula XVI:

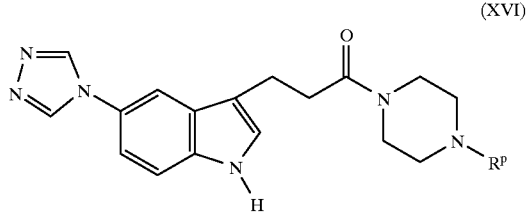

(XVI)

wherein $R^p$ is as defined above; with subsequent removal of the amino-protecting group $R^p$.

Similarly, the compounds according to the invention may be prepared by a process which comprises reducing a compound of formula XVII:

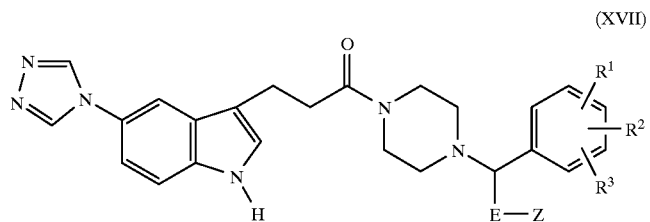

(XVII)

wherein $R^1$, $R^2$, $R^3$, E and Z are as defined above.

The reduction of compound XVI or compound XVII is conveniently effected by treating the appropriate compound with a reducing agent such as lithium aluminium hydride in an appropriate solvent, e.g. diethyl ether or tetrahydrofuran, or mixtures thereof.

The compounds of formulae XVI and XVII above may suitably be prepared by reacting the appropriate compound of formula X or XIII with a compound of formula XVIII:

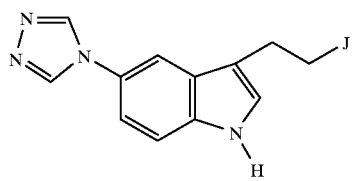

(XVIII)

wherein J represents a reactive carboxylate moiety.

Suitable values for the reactive carboxylate moiety J include esters, for example $C_{1-4}$ alkyl esters; acid anhydrides, for example mixed anhydrides with $C_{1-4}$ alkanoic acids; acid halides, for example acid chlorides; and acylimidazoles.

By way of example, the intermediates of formula XVIII above wherein J is an acid chloride moiety may be prepared by treating the corresponding carboxylic acid derivative with thionyl chloride in toluene. Similarly, the intermediates of formula XVIII wherein J is an acylimidazole moiety may be prepared by treating the corresponding carboxylic acid derivative with 1,1'-carbonyldiimidazole. Alternatively, the reactive carboxylate moiety J may be obtained by treating the corresponding compound wherein J is carboxy with 1-(3-dimethylaminopropyl)-3-ethylcarbodiimide hydrochloride and 1-hydroxybenzotriazole hydrate, optionally in the presence of triethylamine; the resulting activated carboxylate intermediate may then suitably be reacted in situ with the required compound of formula X or XIII.

In a still further procedure, the compounds of formula I above wherein Z represents hydroxy may be prepared by a process which comprises reducing a compound of formula XIX:

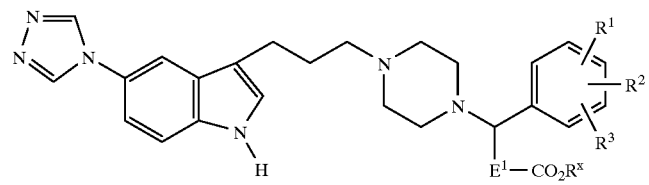

(XIX)

wherein $E^1$ represents a chemical bond or a straight or branched alkylene chain containing from 1 to 3 carbon atoms, $R^x$ represents $C_{1-6}$ alkyl, and $R^1$, $R^2$ and $R^3$ are as defined above.

The reduction of the ester functionality in compound XIX may conveniently be effected by treatment with a reducing agent such as lithium aluminium hydride, typically in a solvent such as tetrahydrofuran.

In a yet further procedure, the compounds of formula I above wherein Z represents imidazol-1-yl, pyrrolidin-1-yl, oxazol-2-on-3-yl or oxazolidin-2-on-3-yl may be prepared by a process which comprises reacting a compound of formula XX with a compound of formula XXI:

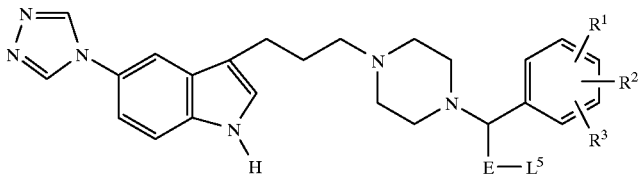 

(XX) (XXI)

wherein $Z^2$ represents imidazol-1-yl, pyrrolidin-1-yl, oxazol-2-on-3-yl or oxazolidin-2-on-3-yl, $L^5$ represents a suitable leaving group, and $R^1$, $R^2$, $R^3$ and E are as defined above.

The leaving group $L^5$ suitably represents mesyloxy or tosyloxy.

Where $Z^2$ represents an oxazol-2-on-3-yl moiety, compound XXI is desirably treated with a strong base such as sodium hydride, in order to generate the anion thereof prior to reaction with compound XX. In this context, a suitable solvent is N,N-dimethylformamide, and the reaction is typically carried out at room temperature. Otherwise, the reaction between compounds XX and XXI can be effected in the absence of added base, and will conveniently be accomplished in tetrahydrofuran as solvent, at an elevated temperature under sealed tube conditions.

Where the leaving group $L^5$ is mesyloxy or tosyloxy, the intermediate of formula XX may conveniently be prepared by mesylation or tosylation respectively of the corresponding compound of formula I wherein Z is hydroxy. The latter compound may conveniently be prepared by reduction of the appropriate compound of formula XIX as described above.

The hydrazine derivative of formula VI above can be prepared by the method described in WO 94/03446, as also can the aniline derivative of formula XV.

Where they are not commercially available, the starting materials of formula IV, V, IX, X, XIII, XVIII, XIX and XXI may be prepared by methods analogous to those described in the accompanying Examples, or by standard procedures well known from the art.

It will be appreciated that any compound of formula I initially obtained from any one of the above processes may, where appropriate, subsequently be elaborated into a further compound of formula I using techniques known from the art. For example, a compound of formula I wherein Z is hydroxy initially obtained may be converted into the corresponding compound wherein Z is amino by mesylation of the hydroxy group with mesyl chloride under standard conditions, followed by treatment with ammonia in methanol/tetrahydrofuran in a sealed tube at an elevated temperature; the resulting amino compound can then be treated with 2-chloroethyl chloroformate to yield the respective chloroethyl carbamate derivative, with subsequent ring closure by treatment with sodium hydride to afford the desired compound of formula I wherein Z represents an oxazolidin-2-on-3-yl moiety.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (-)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with the present invention potently and selectively bind to the 5-$HT_{1D\alpha}$ receptor subtype, inhibit forskolin-stimulated adenylyl cyclase activity, and stimulate [$^{35}$S]-GTPγS binding to membranes from clonal cell lines expressing human cloned receptors.

5-$HT_{1D\alpha}$/5-$HT_{1D\beta}$ Radioligand Binding

Chinese hamster ovary (CHO) clonal cell lines expressing the human 5-$HT_{1D\alpha}$ and 5-$HT_{1D\beta}$ receptors were harvested in PBS and homogenised in ice cold 50 mM Tris-HCl (pH 7.7 at room temperature) with a Kinematica polytron and centrifuged at 48,000 g at 4° C. for 11 min. The pellet was then resuspended in 50 mM Tris-HCl followed by a 10 min incubation at 37° C. Finally the tissue was recentrifuged at 48,000 g, 4° C. for 11 min and the pellet resuspended, in assay buffer (composition in mM: Tris-HCl 50, pargyline 0.01, $CaCl_2$ 4; ascorbate 0.1%; pH 7.7 at room temperature) to give the required volume immediately prior to use (0.2 mg protein/ml). Incubations were carried out for 30 min at 37° C. in the presence of 0.02–150 nM [$^3$H]-5-HT for saturation studies or 2–5 nM [$^3$H]-5-HT for displacement studies. The final assay volume was 1 ml. 5-HT (10 μM) was used to define non-specific binding. The reaction was initiated by the addition of membrane and was terminated by rapid filtration through Whatman GF/B filters (presoaked in 0.3% PEI/0.5% Triton X) followed by 2×4 ml washings with 50 mM Tris-HCl. The radioactive filters were then counted on a LKB beta or a Wallac beta plate counter. Binding parameters were determined by non-linear, least squares regression analysis using an iterative curve fitting routine, from which $IC_{50}$ (the molar concentration of compound necessary to inhibit binding by 50%) values could be calculated for each test compound. The $IC_{50}$ values for binding to the 5-$HT_{1D\alpha}$ receptor subtype obtained for the compounds of the accompanying Examples were below 50 nM in each case. Furthermore, the compounds of the accompanying Examples were all found to possess a selective affinity for the 5-HT$_{1D\alpha}$ receptor subtype of at least 10-fold relative to the 5-HT$_{1D\beta}$ subtype.

5-HT$_{1D\alpha}$/5-HT$_{1D\beta}$ Adenylyl Cyclase Assay

Studies were performed essentially as described in *J. Pharmacol. Exp. Ther.*, 1986, 238, 248. CHO clonal cell lines expressing the human cloned 5-HT$_{1D\alpha}$ and 5-HT$_{1D\beta}$ receptors were harvested in PBS and homogenised, using a motor driven teflon/glass homogeniser, in ice cold Tris HCl-EGTA buffer (composition in mM: Tris HCl 10, EGTA 1, pH 8.0 at room temperature) and incubated on ice for 30–60 min. The tissue was then centrifuged at 20,000 g for 20 min at 4° C., the supernatant discarded and the pellet resuspended in Tris HCl-EDTA buffer (composition in mM: Tris HCl 50, EDTA 5, pH 7.6 at room temperature) just prior to assay. The adenylyl cyclase activity was determined by measuring the conversion of α-[$^{33}$P]-ATP to [$^{33}$P]-cyclic AMP. A 10 μl aliquot of the membrane suspension was incubated, for 10–15 min, in a final volume of 50 μl, at 30° C., with or without forskolin (10 μM), in the presence or absence of test compound. The incubation buffer consisted of 50 mM Tris HCl (pH 7.6 at room temperature), 100 mM NaCl, 30 μM GTP, 50 μM cyclic AMP, 1 mM dithiothreitol, 1 mM ATP, 5 mM MgCl$_2$, 1 mM EGTA, 1 mM 3-isobutyl-1-methylxanthine, 3.5 mM creatinine phosphate, 0.2 mg/ml creatine phosphokinase, 0.5–1 μCi α-[$^{33}$P]-ATP and 1 nCi [$^3$H]-cyclic AMP. The incubation was initiated by the addition of membrane, following a 5 min preincubation at 30° C., and was terminated by the addition of 100 μl SDS (composition in mM: sodium lauryl sulphate 2%, ATP 45, cyclic AMP 1.3, pH 7.5 at room temperature). The ATP and cyclic AMP were separated on a double column chromatography system (*Anal. Biochem.*, 1974, 58, 541). Functional parameters were determined using a least squares curve fitting programme ALLFIT (*Am. J. Physiol.*, 1978, 235, E97) from which E$_{max}$ (maximal effect) and EC$_{50}$ (the molar concentration of compound necessary to inhibit the maximal effect by 50%) values were obtained for each test compound. Of those compounds which were tested in this assay, the EC$_{50}$ values for the 5-HT$_{1D\alpha}$ receptor obtained for the compounds of the accompanying Examples were below 500 nM in each case. Moreover, the compounds of the accompanying Examples which were tested were all found to possess at least a 10-fold selectivity for the 5-HT$_{1D\alpha}$ receptor subtype relative to the 5-HT$_{1D\beta}$ subtype.

5-HT$_{1D\alpha}$/5-HT$_{1D\beta}$ GTPγS Binding

Studies were performed essentially as described in *Br. J. Pharmacol.*, 1993, 109, 1120. CHO clonal cell lines expressing the human cloned 5-HT$_{1D\alpha}$ and 5-HT$_{1D\beta}$ receptors were harvested in PBS and homogenised using a Kinematica polytron in ice cold 20 mM HEPES containing 10 mM EDTA, pH 7.4 at room temperature. The membranes were then centrifuged at 40,000 g, 4° C. for 15 min. The pellet was then resuspended in ice cold 20 mM HEPES containing 0.1 mM EDTA, pH 7.4 at room temperature and recentrifuged at 40,000 g, 4° C. for 15–25 minutes. The membranes were then resuspended in assay buffer (composition in mM: HEPES 20, NaCl 100, MgCl$_2$ 10, pargyline 0.01; ascorbate 0.1%; pH 7.4 at room temperature) at a concentration of 40 μg protein/ml for the 5-HT$_{1D\alpha}$ receptor transfected cells and 40–50 μg protein/ml for the 5-HT$_{1D\beta}$ receptor transfected cells. The membrane suspension was then incubated, in a volume of 1 ml, with GDP (100 μM for 5-HT$_{1D\alpha}$ receptor transfected cells, 30 μM for the 5-HT$_{1D\beta}$ receptor transfected cells) and test compound at 30° C. for 20 min and then transferred to ice for a further 15 min. [$^{35}$S]-GTPγS was then added at a final concentration of 100 pM and the samples incubated for 30 min at 30° C. The reaction was initiated by the addition of membrane and was terminated by rapid filtration through Whatman GF/B filters and washed with 5 ml water. The radioactive filters were then counted on a LKB beta counter. Functional parameters were determined by a non-linear, least squares regression analysis using an iterative curve fitting routine, from which E$_{max}$ (maximal effect) and EC$_{50}$ (the molar concentration of compound necessary to inhibit the maximal effect by 50%) values were obtained for each test compound. Of those compounds which were tested in this assay, the EC$_{50}$ values for the 5-HT$_{1D\alpha}$ receptor obtained for the compounds of the accompanying Examples were below 500 nM in each case. Moreover, the compounds of the accompanying Examples which were tested were all found to possess at least a 10-fold selectivity for the 5-HT$_{1D\alpha}$ receptor subtype relative to the 5-HT$_{1D\beta}$ subtype.

EXAMPLE 1

1-[3-(5-(1,2,4-Triazol-4-yl)-1H-indol-3-yl)propyl]-4-[3-hydroxy-1-phenylpropyl]piperazine. 1.9 Hydrogen Oxalate Intermediate 1

4-(1,2,4-Triazol-4-yl)phenylhydrazine

Prepared as described in WO 94/03446, Example 1.

Intermediate 2

1-(3-[5-(1,2,4-Triazol-4-yl)-1H-indol-3-yl]propyl)-4-(H)-piperazine. 3.5 Hydrogen Oxalate 1. 5-[4-(tert-Butyloxycarbonyl)piperazin-1-yl]pentanal dimethyl acetal a) 5-Bromopentanal dimethyl acetal To a solution of 5-bromovaleryl chloride (50 g, 0.251 mol) in anhydrous THF (500 ml), at −78° C., was added lithium tri-tert-butoxyaluminohydride (1.0M solution in tetrahydrofuran, 300 ml; 0.30 mol), keeping the temperature below −70° C. The solution was stirred at −78° C. for 5 h and then quenched by dropwise addition of 2M hydrochloric acid (350 ml). The mixture was warmed to room temperature and stirred for 16 h. Diethyl ether (500 ml) was added, the aqueous phase separated and extracted further with ether (×2). The combined extracts were washed with saturated Na$_2$CO$_3$ solution (×1), water (×1) and brine (×2), dried (Na$_2$SO$_4$) and evaporated to give 5-bromovaleraldehyde (37.5 g, 91%). A solution of 5-bromovaleraldehyde (37.5 g, 0.227 mol) in methanol (250 ml) and concentrated sulphuric acid (0.5 ml) was stirred at room temperature for 3 h. The solvent was removed under vacuum and to the residue was added K$_2$CO$_3$ solution (50 ml) and diethyl ether (500 ml). The aqueous layer was separated and re-extracted with ether (×2). The combined extracts were washed with water and brine, dried (Na$_2$SO$_4$) and evaporated. The crude product was chromatographed on silica gel eluting with diethyl ether/hexane (1:9) to give the title-acetal (27.5 g, 57%). δ(250 MHz, CDCl$_3$) 1.43–1.67 (4H, m, 2 of CH$_2$); 1.83–1.94 (2H, m, CH$_2$); 3.38 (6H, s, CH(OMe)$_2$); 3.42 (2H, t, J=7 Hz, CH$_2$Br), 4.37 (1H, t, J=7 Hz, C$\underline{H}$(OMe)$_2$).

b) 5-[4-(tert-Butyloxycarbonyl)piperazin-1-yl]pentanal dimethyl acetal

A mixture of 5-bromovaleraldehyde dimethyl acetal (27.5 g, 0.13 mol), Na$_2$CO$_3$ (20.7 g, 0.195 mol), sodium iodide (19.5 g, 0.13 mol) and tert-butyl-1-piperazinecarboxylate (25.5 g, 0.137 mol), in dimethoxyethane (250 ml), was heated at 100° C. for 3 h. Aluminium foil was wrapped around the vessel to exclude light. The mixture was cooled to room temperature and filtered. The filtrate was evaporated under reduced pressure and then EtOAc (50 ml) added and the mixture filtered again to remove inorganic salts. The solvent was removed under vacuum and the residue chromatographed on silica gel eluting with EtOAc to give the title-product (25.7 g, 63%). δ(250 MHz, CDCl$_3$) 1.29–1.71 (6H, m, 3 of CH$_2$); 1.46 (9H, s, OC(Me)$_3$); 2.31–2.39 (6H, m, 3 of CH$_2$); 3.32 (6H, s, CH(OMe)$_2$); 3.41–3.45 (4H, m, 2 of CH$_2$); 4.36 (1H, t, J=6 Hz, CH(OMe)$_2$).

2. 1-(3-[5-(1,2,4-Triazol-4-yl)-1H-indol-3-yl]propyl)-4-(H)-piperazine. 3.5 Hydrogen Oxalate A mixture of Intermediate 1 (5.0 g, 28.6 mmol) and 5-[4-(tert-butyloxycarbonyl)piperazin-1-yl]pentanal dimethylacetal (9.03 g, 28.6 mmol) in 4% sulphuric acid (150 ml) was heated at reflux for 48 h. The solution was cooled in an ice-bath, basified with solid K$_2$CO$_3$ and extracted with butan-1-ol (×3). The solvent was removed under vacuum and azeotroped with hexane (×2). The crude product was purified by chromatography on silica gel eluting with CH$_2$Cl$_2$/MeOH/NH$_3$ (30:8:1) to give the title-indole (3.9 g, 44%). The 3.5 hydrogen oxalate salt was prepared using 200 mg of free base: mp 90–92° C. (Found: C, 45.97; H, 4.76; N, 13.77. C$_{17}$H$_{22}$N$_6$.3.5(C$_2$H$_2$O$_4$) requires C, 46.08; H, 4.76; N, 13.43%); δ(360 MHz, D$_2$O) 2.12–2.24 (2H, m, CH$_2$); 2.93 (2H, t, J=7 Hz, CH$_2$); 3.46–3.76 (8H, m, 4 of CH$_2$); 7.37 (1H, dd, J=1.9 and 8.7 Hz, Ar—H); 7.39 (1H, s, Ar—H); 7.66 (1H, d, J=8.7, Ar—H); 7.82 (1H, d, J=1.9 Hz, Ar—H); 9.13 (2H, s, Triazole-H).

Step 1

3-Bromo-3-phenylpropan-1-ol

To a solution of 3-phenylpropan-1-ol (5 mL, 0.037 mol) in CCl$_4$ (60 mL) was added N-bromosuccinimide (6.5 g, 0.037 mol) and benzoyl peroxide (383 mg of 70% technical grade, 1.1 mmol). The mixture was heated at reflux for 3 h, after which time the solution was cooled and filtered. The filtrate was removed in vacuo and the residue partitioned between Et$_2$O (100 mL) and water (100 mL). The organic layer was separated, dried (Na$_2$SO$_4$) and evaporated. The residue was chromatographed on silica gel, eluting with petrol:EtOAc (2:1), to give the bromide (3.7 g, 47%) as a colourless oil. $^1$H NMR (250 MHz, CDCl$_3$) δ2.13–2.26 (1H, m), 2.36–2.49 (1H, m), 3.40–3.53 (2H, m), 5.36 (1H, dd, J=8.9 and 5.9 Hz), 7.27–7.49 (5H, m).

Step 2

1-[3-(5-(1,2,4-Triazol-4-yl)-1H-indol-3-yl)propyl]-4-[3-hydroxy-1-phenylpropyl]piperazine. 1.9 Hydrogen Oxalate A solution of Intermediate 2 (250 mg, 0.81 mmol), 3-bromo-3-phenylpropan-1-ol (191 mg, 0.89 mmol) and K$_2$CO$_3$ (111 mg, 0.81 mmol) in DMF (7 mL) was heated at 70° C. for 2 h. After this time more bromide (38 mg, 0.17 mmol) was added and heating continued for a further 2 h. The solvent was then removed in vacuo and the residue partitioned between CH$_2$Cl$_2$ (2×20 mL) and water (20 mL). The combined organic layers were dried (Na$_2$SO$_4$) and evaporated. The residue was chromatographed on silica gel, eluting with CH$_2$Cl$_2$:MeOH:NH$_3$ (95:5:1), to afford the title piperazine (228 mg, 64%) as a colourless oil. The hydrogen oxalate salt was prepared. mp. 153° C. C$_{26}$H$_{32}$N$_6$O. 1.9 (C$_2$H$_2$O$_4$) requires: C, 58.14; H, 5.86; N, 13.65%. Found: C, 57.79; H, 5.85; N, 13.92%. $^1$H NMR (360 MHz, d$_6$-DMSO) δ1.79–1.87 (1H, m), 1.88–2.01 (2H, m), 2.04–2.15 (1H, m), 2.59–2.80 (4H, m), 2.82–3.39 (10H, m), 3.70–3.77 (1H, m), 7.24–7.36 (7H, m), 7.49 (1H, d, J=8.5 Hz), 7.77 (1H, s), 8.99 (2H, s), 11.16 (1H, br s). MS (ES$^+$) (445, M+1).

EXAMPLE 2

1-[3-(5-(1,2,4-Triazol-4-yl)-1H-indol-3-yl)propyl]-4-[1-(4-fluorophenyl)-3-hydroxypropyl]piperazine. 1.5 Hydrogen Oxalate Step 1

Ethyl 3-(4-fluorophenyl)prop-2-enoate

A solution of 4-fluorobenzaldehyde (8.6 mL, 0.081 mol) and carboethoxymethylene triphenylphosphorane (34 g, 0.097 mol) in toluene (400 mL) was heated at reflux for 3 h. After this time the solvent was removed in vacuo and the residue triturated in petrol:Et$_2$O (1:1). The mixture was filtered and the filtrate evaporated. The residue was chromatographed on silica gel, eluting with petrol:Et$_2$O (3:1), to afford the ester (14.4 g, 92%) as a low-melting colourless solid. $^1$H NMR (major isomer) (250 MHz, CDCl$_3$) δ1.34 (3H, t, J=7.0 Hz), 4.26 (2H, q, J=7.0 Hz), 6.36 (1H, d, J=16 Hz), 7.07 (2H, dd, J$_{HA-HB}$=8.6 Hz and J$_{HA-F}$=8.6 Hz), 7.51 (2H, dd, J$_{HB-HA}$=8.6 Hz and J$_{HB-F}$=5.3 Hz), 7.65 (1H, d, J=16 Hz).

Step 2

3-Bromo-3-(4-fluorophenyl)propan-1-ol

A solution of the alkene (14.4 g, 0.074 mol) in EtOH (200 mL) containing 10% Pd on C (1.0 g) was hydrogenated at 40 psi for 40 min. After this time the catalyst was removed by filtration and the filtrate evaporated. The residue was azeotroped with EtOH (50 mL) and the crude ester (14 g) isolated as a colourless oil and used directly without further purification.

To a stirred solution of the saturated ester (14 g) in THF (300 mL) at −10° C., under nitrogen, was added LiAlH$_4$ (78 mL of a 1.0M solution in Et$_2$O, 78 mmol) dropwise. After addition was complete the solution was stirred for a further 1 h at 0° C. A solution of Na$_2$SO$_4$ (sat., 50 mL) was added and the solid removed by filtration. The filtrate was removed in vacuo and the residue partitioned between Et$_2$O (200 mL) and water (200 mL). The organic layer was separated, dried (Na$_2$SO$_4$) and evaporated. The crude 3-(4-fluorophenyl)propan-1-ol (11 g) was isolated as a colourless oil and used directly without further purification. To a solution of the alcohol (5 g, prepared from above) in CCl$_4$ (100 mL) was added N-bromosuccinimide (5.8 g, 0.032 mol) and benzoyl peroxide (331 mg of 70% technical grade, 0.96 mmol). The mixture was heated at reflux for 3 h then the solution was cooled to room temperature and filtered. The filtrate was evaporated and the residue chromatographed on silica gel, eluting with petrol:Et$_2$O (2:1→1:1). The bromide (3.52 g, 47%) was isolated as a pale yellow oil. $^1$H NMR (250 MHz, CDCl$_3$) δ2.23–2.36 (1H, m), 2.41–2.55 (1H, m), 3.67–3.90 (2H, m), 5.22 (1H, dd, J=9.3 and 5–7 Hz), 7.04 (2H, dd, J$_{HA-HB}$=8.6 Hz and J$_{HA-F}$=8.6 Hz), 7.39 (2H, dd, J$_{HB-HA}$=8.6 Hz and J$_{HB-F}$=5.3 Hz).

Step 3

1-[3-(5-(1,2,4-Triazol-4-yl)-1H-indol-3-yl)propyl]-4-[1-(4-fluorophenyl)-3-hydroxypropyl]piperazine. 1.5 Hydrogen Oxalate Prepared as described in Example 1, Step 2 using Intermediate 2 (381 mg, 1.22 mmol), 3-bromo-3-(4-fluorophenyl)propan-1-ol (369 mg, 1.59 mmol), K$_2$CO$_3$ (168 mg, 1.22 mmol) and DMF (9 mL). The crude residue was chromatographed on silica gel, eluting with CH$_2$Cl$_2$:MeOH (95:5→90:10), to afford the title piperazine (411 mg, 73%) as a pale yellow oil. The hydrogen oxalate salt was prepared. mp. 134° C. C$_{26}$H$_{31}$N$_6$OF. 1.5 (C$_2$H$_2$O$_4$). H$_2$O requires: C, 56.58; H, 5.89; N, 13.65%. Found C, 56.28; H, 6.05; N, 13.44%. $^1$H NMR (250 MHz, d$_6$-DMSO) δ1.70–2.13 (4H, m), 2.64–3.39 (14H, m), 3.72–3.76 (1H, m), 7.15 (2H, dd, J$_{HA-HB}$=8.9 Hz and J$_{HA-F}$=8.9 Hz), 7.22–7.30 (4H, m), 7.45 (1H, d, J=8.6 Hz), 7.73 (1H, d, J=2.0 Hz), 8.97 (2H, s), 11.15 (1H, br s). MS (ES$^+$) (463, M+1).

EXAMPLE 3

1-[3-(5-(1,2,4-Triazol-4-yl)-1H-indol-3-yl)propyl]-4-[1-(4-fluorophenyl)-3-methoxypropyl]-piperazine. 1.5 Hydrogen Oxalate Step 1

3-Bromo-3-(4-fluorophenyl)-1-methoxypropane

To a stirred solution of 3-(4-fluorophenyl)propan-1-ol (800 mg, 5.2 mmol) (see Example 2, Step 2) in DMF (20 mL), under nitrogen, was added sodium hydride (250 mg of a 60% dispersion in mineral oil, 6.24 mmol). The mixture was stirred at 0° C. for 20 min then iodomethane (389 μL, 6.24 mmol) was added. Stirring was continued for 30 min then the cooling bath was removed and the mixture stirred at room temperature for 1 h. After this time more sodium hydride (125 mg of a 60% dispersion in mineral oil, 3.1 mmol) followed by iodomethane (195 μL, 3.1 mmol) were added and the mixture stirred for a further 2 h. The solvent was removed in vacuo and the residue partitioned between ether (2×50 mL) and water (50 mL). The combined organic layers were dried (Na$_2$SO$_4$) and evaporated. The crude methyl ether (593 mg), which was isolated as a colourless oil, was used in the subsequent reaction without further purification.

To a solution of the ether (590 mg) (prepared as described above) in CCl$_4$ (20 mL) was added N-bromosuccinimide (625 mg, 3.51 mmol) and benzoyl peroxide (36 mg of 70% technical grade, 0.1 mmol). The mixture was heated at reflux for 1 h then the solution was cooled to room temperature and filtered. The filtrate was removed in vacuo and the residue chromatographed on silica gel, eluting with petrol:Et$_2$O (8:1). The bromide (304 mg, 35%) was isolated as a colourless oil. $^1$H NMR (250 MHz, CDCl$_3$) δ2.22–2.36 (1H, m), 2.40–2.55 (1H, m), 3.33 (3H, s), 3.36–3.43 (1H, m), 3.49–3.58 (1H, m), 5.17 (1H, dd, J=6.0 and 9.0 Hz), 7.02 (2H, dd, J$_{HA-HB}$=8.6 Hz and J$_{HA-F}$=8.6 Hz), 7.38 (2H, dd, J$_{HB-HA}$=8.6 Hz and J$_{HB-F}$=5.2 Hz).

Step 2

1-[3-(5-(1,2,4-Triazol-4-yl)-1H-indol-3-yl)propyl]-4-[1-(4-fluorophenyl)-3-methoxyproyl]piperazine. 1.5 Hydrogen Oxalate Prepared as described in Example 1, Step 2 using Intermediate 2 (200 mg, 0.65 mmol), 3-bromo-3-(4-fluorophenyl)-1-methoxypropane (237 mg, 0.96 mmol), K$_2$CO$_3$ (89 mg, 0.65 mmol) and DMF (10 mL). The crude residue was chromatographed on silica gel, eluting with CH$_2$Cl$_2$:MeOH:NH$_3$ (90:10:0→90:10:1), to afford the title piperazine (163 mg, 53%) as the free base. The hydrogen oxalate salt was prepared. mp. 166° C. C$_{27}$H$_{33}$N$_6$FO. 1.5 (C$_2$H$_2$O$_4$). 1.2(H$_2$O) requires: C, 56.90; H, 6.11; N, 13.27%. Found: C,57.23; H, 6.46; N, 13.07%. $^1$H NMR (360 MHz, d$_6$-DMSO)δ1.83–2.05 (3H, m), 2.13–2.22 (1H, m), 2.67–3.35 (17H, m), 3.70–3.74 (1H, m), 7.18 (2H, dd, J$_{HA-HB}$=8.8 Hz and J$_{HA-F}$=8.8 Hz), 7.28–7.32 (4H, m), 7.49 (1H, d, J=8.5 Hz), 7.77 (1H, d, J=1.9 Hz), 8.99 (2H, s), 11.15 (1H, br s). MS (ES$^+$) (477, M+1).

EXAMPLE 4

1-[3-(5-(1,2,4-Triazol-4-yl)-1H-indol-3-yl)propyl]-4-[3-(5-methyl-1,2,4-oxadiazol-3-yl)-1-phenylpropyl] piperazine. 1.5 Hydrogen Oxalate Intermediate 3

3-[5-(1,2,4-Triazol-4-yl)-1H-indol-3-yl]propan-1-ol

A solution of Intermediate 1 (25 g, 143 mmol) in dioxan (250 mL) was treated with dihydropyran (24 g, 286 mmol) followed by 1M hydrochloric acid (150 mL) and heated at reflux for 18 h. The mixture was evaporated then azeotroped with toluene. Inorganic solids were removed by treating the residue with a mixture of methanol and acetonitrile. The mother liquors were chromatographed on silica gel, eluting with CH$_2$Cl$_2$:MeOH (9:1→4:1). The compound was recrystallised from acetonitrile to afford the title alcohol (10.24 g, 30%) as a colourless solid. mp. 205–207° C. $^1$H NMR (360 MHz, d$_6$-DMSO) δ1.81 (2H, quin, J=7.0 Hz), 2.75 (2H, t, J=8.0 Hz), 3.46 (2H, dt, J=6.0 and 5.0 Hz), 4.43 (1H, t, J=5.0 Hz), 7.26 (1H, d, J=2.0 Hz), 7.29 (1H, dd, J=9.0 and 2.0 Hz), 7.47 (1H, d, J=9.0 Hz), 7.77 (1H, d, J=2.0 Hz), 9.01 (2H, s), 11.05 (1H, br s). MS (CI$^+$) (243, M+1).

Step 1

4-Bromo-4-phenylbutyronitrile

Prepared as described in Example 1, Step 1 using 4-phenylbutyronitrile (5.2 mL, 0.034 mol), N-bromosuccinimide (6.65 g, 0.037 mol), benzoyl peroxide (352 mg of 70% technical grade. 1.0 mmol) and CCl$_4$ (60 mL). The crude residue was chromatographed on silica gel, eluting with petrol:Et$_2$O (3:1). The bromide (5.62 g, 74%) was isolated as a colourless oil. $^1$H NMR (250 MHz, CDCl$_3$) δ2.36–2.64 (4H, m), 5.00–5.07 (1H, m), 7.29–7.43 (5H, m).

Step 2

4-(4-tert-Butyloxycarbonylpiperazinyl)-4-phenylbutyronitrile

A solution of 1-(tert-butyloxycarbonyl)piperazine (1.73 g, 9.3 mmol), 4-bromo-4-phenylbutyronitrile (2.5 g, 11 mmol) and K$_2$CO$_3$ (1.4 g, 10.2 mmol) in DMF (40 mL) was heated at 60° C. for 4 h. After this time the mixture was cooled to room temperature, filtered and the filtrate evaporated. The residue was partitioned between EtOAc (100 mL) and water (100 mL). The organic layer was separated, dried (Na$_2$SO$_4$) and evaporated. The residue was chromatographed on silica gel, eluting with petrol:EtOAc (2:1). The piperazine (2.69 g, 88%) was isolated as a pale yellow oil, which solidified on standing in the fridge. $^1$H NMR (250 MHz, CDCl$_3$) δ1.41 (9H, s), 1.94–2.46 (8H, m), 3.32–3.60 (5H, m), 7.15–7.42 (5H, m). MS (ES$^+$) (330, M+1).

Step 3

4-(4-tert-Butyloxycarbonylpiperazinyl)-4-phenylbutyl carboxamide Oxime

To a solution of sodium methoxide in MeOH (183 mg sodium in 25 mL MeOH, 8.0 mmol) was added hydroxylamine hydrochloride (0.55 g, 8.0 mmol). The mixture was stirred at room temperature for 15 min then 4-(4-tert-butyloxycarbonylpiperazinyl)-4-phenylbutyronitrile (2.62 g, 8.0 mmol) was added. The mixture was heated at reflux for 16 h then the solution was cooled to room temperature. The mixture was filtered, evaporated and the residue partitioned between EtOAc (60 mL) and water (60 mL). The organic layer was separated, dried (Na$_2$SO$_4$) and evaporated in vacuo. The residue was chromatographed on silica gel, eluting with CH$_2$Cl$_2$:MeOH (90:10), to afford the amide oxime (934 mg, 32%). $^1$H NMR (360 MHz, d$_6$-DMSO) δ1.34 (9H, s), 1.73–2.30 (8H, m), 3.19–3.30 (4H, m), 3.39–3.45 (1H, m), 5.32 (2H, br s), 7.19–7.36 (5H, m), 8.70 (1H, s).

Step 4

3-[3-[4-(tert-Butyloxycarbonyl)piperazin-1-yl]-3-phenyl]propyl-5-methyl-1,2,4-oxadiazole To a solution of sodium methoxide in MeOH (59 mg sodium in 20 mL MeOH, 2.56 mmol) at room temperature was added the amide oxime (0.93 g, 2.56 mmol) followed by EtOAc (1.25 mL). The mixture was heated at reflux for 2 days before more sodium (30 mg, 1.3 mmol) was added. Heating was continued for one further day before the addition of more sodium (30 mg, 1.3 mmol) followed by EtOAc (1.25 mL). Heating at reflux was continued for 3 days before more sodium (30 mg, 1.3 mmol) and EtOAc (1.25 mL) were added. After heating for a further 2 days the solution was cooled to room temperature and the solvent evaporated. The residue was partitioned between EtOAc (20 mL) and water (2×20 mL). The organic phase was separated, dried (Na$_2$SO$_4$) and evaporated. The residue was chromatographed on silica gel, eluting with petrol:EtOAc (1:1→0:1). The oxadiazole (783 mg, 79%) was isolated as a colourless oil. $^1$H NMR (360 MHz, CDCl$_3$) δ1.41 (9H, s), 2.08–2.42 (6H, m), 2.53 (3H, s), 2.59–2.70 (2H, m), 3.31–3.48 (5H, m), 7.20–7.38 (5H, m).

Step 5

1-[3-(5-(1,2,4-Triazol-4-yl)-1H-indol-3-yl)propyl]-4-[3-(5-methyl-1,2,4-oxadiazol-3-yl)-1-phenylpropyl]piperazine. 1.5 Hydrogen Oxalate A solution of the oxadiazole (390 mg, 1.0 mmol) in CH$_2$Cl$_2$ (20 mL) and trifluoroacetic acid (4 mL) was stirred at room temperature overnight. The solvent was removed in vacuo and the residue partitioned between CH$_2$Cl$_2$ (2×20 mL) and aqueous K$_2$CO$_3$ (10%, 20 mL). The combined organic layers were dried (Na$_2$SO$_4$) and evaporated. The crude amine (276 mg) was used without further purification.

To a solution of Intermediate 3 (150 mg, 0.62 mmol) in THF (80 mL), under nitrogen, at room temperature, was added triethylamine (188 μL, 1.36 mmol) and methanesulphonyl chloride (105 μL, 1.36 mmol). After stirring for 1 h more triethylamine (60 μL, 0.43 mmol) followed by methanesulphonyl chloride (30 μL, 0.39 mmol) were added. After stirring for a further 30 min more triethylamine (30 μL, 0.21 mmol) and methanesulphonyl chloride (15 μL, 0.20 mmol) were added. After a further 30 min the solution was filtered and the filtrate evaporated in vacuo. The crude mesylate was used in the subsequent reaction without further purification.

To a solution of the crude mesylate in iso-propanol (25 mL) was added the crude amine (276 mg, prepared as described above), sodium iodide (93 mg, 0.62 mmol) and K$_2$CO$_3$ (297 mg, 1.43 mmol). The mixture was heated at reflux for 4 h. The solution was then cooled and filtered and the filtrate evaporated. The residue was partitioned between CH$_2$Cl$_2$ (2×20 mL) and water (20 mL) and the combined organic layers dried (Na$_2$SO$_4$) and evaporated. The residue was chromatographed on silica gel, eluting with CH$_2$Cl$_2$:MeOH:NH$_3$ (95:5:0→90:10:0→90:10:1). The title piperazine (196 mg, 62%) was isolated as a cream-coloured foam. The hydrogen oxalate salt was prepared. mp. 134° C. C$_{29}$H$_{34}$N$_8$O. 1.5(C$_2$H$_2$O$_4$). 0.5(H$_2$O) requires: C, 58.71; H, 5.85; N, 17.12%. Found: C, 58.65; H, 6.20; N, 16.82%. $^1$H NMR (360 MHz, d$_6$-DMSO) δ1.90–2.10 (3H, m), 2.26–2.40 (1H, m), 2.42–3.30 (17H, m), 3.57–3.63 (1H, m), 7.25–7.40 (7H, m), 7.49 (1H, d, J=8.6 Hz), 7.77 (1H, s), 8.99 (2H, s), 11.16 (1H, br s). MS (ES$^+$) (511, M+1).

EXAMPLE 5

1-[3-(5-(1,2,4-Triazol-4-yl)-1H-indol-3-yl)propyl]-4-[1-(4-fluorophenyl)-2-hydroxyethyl]piperazine. 1.1 Hydrogen Oxalate Step 1

Methyl 2-bromo-2-(4-fluorophenyl)ethyl acetate

To a stirred solution of thionyl chloride (4.8 mL, 0.066 mol) in MeOH (100 mL) at 0° C., under nitrogen, was added 4-fluorophenylacetic acid (5.1 g, 0.033 mol) portionwise. The cooling bath was removed and the solution stirred at room temperature for 2 h. The solvents were removed in vacuo and the crude methyl ester was isolated as a colourless oil. The ester was used in the subsequent reaction without further purification.

A solution of this ester, N-bromosuccinimide (6.17 g, 0.035 mol) and benzoyl peroxide (342 mg of 70% technical grade, 0.99 mol) in CCl$_4$ (60 mL) was heated at reflux, under nitrogen, for 1 h. After this time the solvent was evaporated and the residue partitioned between ether (100 mL) and water (100 mL). The organic layer was separated, dried (Na$_2$SO$_4$) and evaporated. The residue was chromatographed on silica gel, eluting with petrol:Et$_2$O (3:1), to afford the title bromide (7.33 g, 90%) as a pale yellow oil. $^1$H NMR (250 MHz, CDCl$_3$) δ3.80 (3H, s), 5.34 (1H, s), 7.05 (2H, dd, J$_{HA-HB}$=8.7 Hz and J$_{HA-F}$=8.7 Hz), 7.53 (2H, dd, J$_{HB-HA}$=8.7 Hz and J$_{HB-F}$=5.2 Hz).

Step 2

Methyl 2-(4-fluorophenyl)-2-[1-(3-(5-(1,2,4-triazol-4-yl)-1H-indol-3-yl)propyl)piperazin-4-yl]ethyl acetate In the same was as that described in Example 1, Step 2, using Intermediate 2 (620 mg, 2.0 mmol), methyl 2-bromo-2-(4-fluorophenyl)ethyl acetate (543 mg, 2.2 mmol), K$_2$CO$_3$ (304 mg, 2.2 mmol) and DMF (15 mL). The crude residue was chromatographed on silica gel, eluting with CH$_2$Cl$_2$:MeOH (90:10) to afford the ester (0.85 g, 82%) as a yellow foam. $^1$H NMR (250 MHz, CDCl$_3$) δ1.87–2.03 (2H, m), 2.37–2.71 (10H, m), 2.79 (2H, t, J=7.4 Hz), 3.68 (3H, s), 3.97 (1H, s), 7.03 (2H, dd, J$_{HA-HB}$=8.6 Hz and J$_{HA-F}$=8.6 Hz), 7.12–7.16 (2H, m), 7.38–7.49 (3H, m), 7.55 (1H, dd, J=1.7 Hz), 8.44 (1H, br s), 8.46 (2H, s). MS (ES$^+$) (477, M+1).

Step 3

1-[3-(5-(1,2,4-Triazol-4-yl)-1H-indol-3-yl)propyl]-4-[1-(4-fluorophenyl)-2-hydroxyethyl]piperazine. 1.1 Hydrogen Oxalate To a solution of the methyl ester (785 mg, 1.65 mmol) in THF (30 mL) at −10° C., was added LiAlH$_4$ (1.65 mL of a 1.0M solution in ether, 1.65 mmol) dropwise. The mixture was stirred at −10° C. for 30 min before more LiAlH$_4$ (0.33 mL of a 1.0M solution in ether, 0.33 mmol) was added. After a further 30 min Na$_2$SO$_4$ solution (sat., 2 mL) was added dropwise and the cooling bath removed. The mixture was stirred for 30 min then the undissolved solid was removed by filtration. The filtrate was evaporated and the residue chromatographed on silica gel, eluting with $CH_2Cl_2$:MeOH:$NH_3$ (90:10:0→90:10:1). The alcohol (671 mg, 91%) was isolated as a pale yellow foam. The hydrogen oxalate salt was prepared. mp. 110° C. (dec.). $C_{25}H_{29}N_6OF$. $1.1(C_2H_2O_4)$. $H_2O$ requires: C, 57.76; H, 5.92; N, 14.86%. Found: C, 58.06; H, 6.02; N, 14.54%. $^1H$ NMR (360 MHz, $d_6$-DMSO) δ1.91–2.03 (2H, m), 2.37–3.20 (12H, m), 3.50–3.57 (1H, m), 3.63–3.70 (1H, m), 3.72–3.77 (1H, m), 7.16 (2H, dd, $J_{HA-HB}$=8.8 Hz and $J_{HA-F}$=8.8 Hz), 7.30–7.36 (4H, m), 7.49 (1H, d, J=8.5 Hz), 7.77 (1H, s), 9.00 (2H, s), 11.16 (1H, br s). MS (ES$^+$) (449, M+1).

EXAMPLE 6

1-[3-(5-(1,2,4-Triazol-4-yl)-1H-indol-3-yl)propyl]-4-[1-(4-fluorophenyl)-2-(imidazol-1-yl)ethyl]piperazine. 2.6 Hydrogen Oxalate To a solution of 1-[3-(5-(1,2,4-triazol-4-yl)-1H-indol-3-yl)propyl]-4-[1-(4-fluorophenyl)-2-hydroxyethyl]piperazine (200 mg, 0.45 mmol) in THF (10 mL) at 0° C. was added triethylamine (124 μL, 0.89 mmol) followed by methanesulphonyl chloride (70 μL, 0.89 mmol). The mixture was stirred at 0° C. for 20 min then the mixture filtered and the filtrate transferred to a sealed tube. Imidazole (608 mg, 8.9 mmol) was added and the mixture heated at 70° C. for 1 h. After this time the solvent was evaporated and the residue partitioned between $CH_2Cl_2$ (50 mL) and water (3×40 mL). The organic phase was separated, dried ($Na_2SO_4$) and evaporated. The residue was chromatographed on silica gel, eluting with $CH_2Cl_2$:MeOH:$NH_3$ (90:10:1). The imidazole (72 mg, 32%) was isolated as a pale yellow foam. The hydrogen oxalate salt was prepared. mp. 93° C. (dec.). $C_{28}H_{31}N_8F$. $2.6(C_2H_2O_4)$. $1.1(H_2O)$ requires: C, 52.99; H, 5.14; N, 14.89%. Found: C, 52.76; H, 5.27; N, 15.07%. $^1H$ NMR (360 MHz, $d_6$-DMSO) δ1.97–2.10 (2H, m), 2.49–3.60 (14H, m), 5.70–5.75 (1H, m), 7.10 (1H, s), 7.22 (2H, dd, $J_{HA-HB}$=8.8 Hz and $J_{HA-F}$=8.8 Hz), 7.30–7.36 (2H, m), 7.41–7.46 (3H, m), 7.50 (1H, d, J=8.6 Hz), 7.80 (1H, s), 8.21 (1H, s), 9.01 (2H, s), 11.18 (1H, br s), MS (ES$^+$) (499, M+1).

EXAMPLE 7

1-[3-(5-(1,2,4-Triazol-4-yl)-1H-indol-3-yl)propyl]-4-[1-(4-fluorophenyl)-2-(oxazolidin-2-on-3-yl)ethyl]piperazine. 2.0 Hydrogen Oxalate Step 1

1-[3-(5-(1,2,4-Triazol-4-yl)-1H-indol-3-yl)propyl]-4-[2-amino-1-(4-fluorophenyl)ethyl]piperazine In the same way as that described in Example 6 using 1-[3-(5-(1,2,4-triazol-4-yl)-1H-indol-3-yl)propyl]-4-[1-(4-fluorophenyl)-2-hydroxyethyl]piperazine (113 mg, 0.25 mmol), triethylamine (70 μL, 0.50 mmol), methanesulphonyl chloride (39 μL, 0.50 mmol) and THF (5 mL). The crude mesylate was converted to the amine in the same manner as that used in Example 6, using ammonia (2.5 mL of a 2M solution in MeOH, 5.0 mmol). The amine (60 mg, 53%) was isolated as a pale yellow foam. $^1H$ NMR (250 MHz, CDCl$_3$) δ1.89–2.01 (2H, m), 2.27–2.85 (14H, m), 4.10 (1H, dd, J=10.1 and 3.8 Hz), 7.00 (2H, dd, $J_{HA-HB}$=8.7 Hz and $J_{HA-F}$=8.7 Hz), 7.13–7.16 (2H, m), 7.34 (2H, dd, $J_{HB-HA}$=8.7 Hz and $J_{HB-F}$=5.5 Hz), 7.47 (1H, d, J=8.6 Hz), 7.57 (1H, d, J=1.9 Hz), 8.37 (1H, br s), 8.47 (2H, s). MS (ES$^+$) (448, M+1).

Step 2

1-[3-(5-(1,2,4-Triazol-4-yl)-1H-indol-3-yl)propyl]-4-[2-(2-chloroethylcarbamoyl)-1-(4-fluorophenyl)ethyl]-piperazine To a solution of 1-[3-(5-(1,2,4-triazol-4-yl)-1H-indol-3-yl)propyl]-4-[2-amino-1-(4-fluorophenyl)ethyl]piperazine (60 mg, 0.13 mmol) in dioxane (2 mL) and water (1 mL) was added NaOH (59 μL of a 10%(w/v) aqueous solution, 0.15 mmol), followed by 2-chloroethyl chloroformate (15 μL, 0.14 mmol). The mixture was stirred at room temperature for 45 min then the solution was adjusted to pH 11 using aqeuous NaOH. The mixture was stirred for a further 30 min then the solvent removed in vacuo. The residue was partitioned between EtOAc (2×2 mL) and water (20 mL). The combined organic layers were dried ($Na_2SO_4$) and evaporated. The residue was chromatographed on silica gel, eluting with $CH_2Cl_2$:MeOH (90:10). The carbamate (47 mg, 63%) was isolated as a colourless foam. $^1H$ NMR (250 MHz, CDCl$_3$) δ1.90–2.03 (2H, m), 2.37–2.92 (14H, m), 3.53–3.77 (2H, m), 4.20–4.31 (2H, m), 4.55–4.69 (1H, m), 5.77–5.88 (1H, m), 7.01 (2H, dd, $J_{HA-HB}$=8.7 Hz and $J_{HA-F}$=8.7 Hz), 7.13–7.28 (4H, m), 7.47 (1H, d, J=8.6 Hz), 7.56 (1H, d, J=2.0 Hz), 8.39 (1H, br s), 8.47 (2H, s). MS (ES$^+$) (554/556, M+1).

Step 3

1-[3-(5-(1 2,4-Triazol-4-yl)-1H-indol-3-yl)propyl]-4-[1-(4-fluorophenyl)-2-(oxazolidin-2-on-3-yl)ethyl]piperazine 2.0 Hydrogen Oxalate To a solution of the carbamate (47 mg, 0.085 mmol) in DMF (5 mL) was added sodium hydride (3.4 mg of a 60% dispersion in mineral oil, 0.085 mmol), and the mixture stirred at room temperature for 45 min. The mixture was then partitioned between $CH_2Cl_2$ (2×20 mL) and water (20 mL). The combined organic layers were dried ($Na_2SO_4$) and evaporated. The residue was chromatographed on silica gel, eluting with $CH_2Cl_2$:MeOH:$NH_3$ (90:10:0→90:10:1). The oxazolidinone (15 mg, 34%) was isolated as a colourless gum. The hydrogen oxalate salt was prepared. mp. 128° C. (dec.). $C_{28}H_{32}N_7O_2F$. $2.0(C_2H_2O_4)$. $0.7(H_2O)$ requires: C, 54.11; H, 5.31; N, 13.80%. Found: C, 54.12; H, 5.14; N, 13.73%. $^1H$ NMR (360 MHz, $d_6$-DMSO) δ1.98–2.10 (2H, m), 2.67–3.20 (12H, m), 3.21–3.30 (1H, m), 3.51–3.63 (1H, m), 4.19–4.30 (4H, m), 4.98–5.03 (1H, m), 7.20 (2H, dd, $J_{HA-HB}$=8.9 Hz and $J_{HA-F}$=8.9 Hz), 7.31–7.34 (2H, m), 7.40 (2H, dd, $J_{HB-HA}$=8.7 Hz and $J_{HB-F}$=5.5 Hz), 7.49 (1H, d, J=8.7 Hz), 7.79 (1H, s), 9.01 (2H s), 11.17 (1H, br s). MS (ES$^+$) (518, M+1).

EXAMPLE 8

1-[3-(5-(1,2,4-Triazol-4-yl)-1H-indol-3-yl)propyl]-4-[1-(4-fluorophenyl-2-methoxyethyl]piperazine 1.4 Hydrogen Oxalate Step 1

Methyl 2-(4-tert-butyloxycarbonylpiperazin-1-yl)-2-(4-fluorophenyl)ethyl acetate To a solution of methyl 2-bromo-2-(4-fluorophenyl)ethyl acetate (3.6 g, 14.6 mmol) in DMF (30 mL) was added 1-(tert-butyloxycarbonyl)piperazine (2.71 g, 14.6 mmol) and $K_2CO_3$ (2.41 g, 17.5 mmol). The mixture was heated at 50° C. for 45 min then the solvent was evaporated. The residue was partitioned between EtOAc (150 mL) and water (100 mL). The organic layer was separated, dried ($Na_2SO_4$)

and evaporated. The residue was chromatographed on silica gel, eluting with hexane:EtOAc (4:1→2:1), to afford the title piperazine (4.65 g, 91%) as a yellow oil. $^1$H NMR (360 MHz, d$_6$-DMSO) δ1.37 (9H, s), 2.30–2.36 (4H, m), 3.26–3.31 (4H, m), 3.62 (3H, s), 4.22 (1H, s), 7.20 (2H, dd, J$_{HA-HB}$=8.9 Hz and J$_{HA-F}$=8.9 Hz), 7.42 (2H, dd, J$_{HB-HA}$=8.9 Hz and J$_{HB-F}$=5.6 Hz). MS (ES$^+$) (353, M+1).

Step 2

2-[4-tert-Butyloxycarbonylpiperazin-1-yl]2-[4-fluorophenyl]ethan-1-ol

To a solution of the ester (4.65 g, 13.2 mmol) in THF (100 mL) at −10° C. was added LiAlH$_4$ (13.2 mL of a 1.0M solution in ether, 13.2 mmol) dropwise. After stirring at −10° C. for 1 h Na$_2$SO$_4$ solution (sat., 13.2 mL) was added dropwise and the cooling bath removed. The mixture was stirred for 30 min and the solid removed by filtration. The filtrate was evaporated and the residue chromatographed on silica gel, eluting with EtOAc:petrol (1:1)→EtOAc:MeOH (99:1). The alcohol (4.17 g, 97%) was isolated as a colourless oil. $^1$H NMR (360 MHz, d$_6$-DMSO) δ1.36 (9H, s), 2.24–2.41 (4H, m), 3.20–3.30 (4H, m), 3.42–3.46 (1H, m), 3.61–3.70 (1H, m), 3.74–3.83 (1H, m), 4.52 (1H, t, J=5.3 Hz), 7.13 (2H, dd, J$_{HA-HB}$=8.7 Hz and J$_{HA-F}$=8.7 Hz), 7.31 (2H, dd, J$_{HB-HA}$=8.7 Hz and J$_{HB-F}$=5.7 Hz). MS (ES$^+$) (325, M+1).

Step 3

4-(tert-Butyloxycarbonyl)-1-[1-(4-fluorophenyl)-2-methoxyethyl]piperazine

To a solution of the alcohol in DMF (20 mL) at 0° C., was added sodium hydride (204 mg of a 60% dispersion in oil, 5.1 mmol). After stirring at 0° C. for 20 min iodomethane (0.32 mL, 5.1 mmol) was added and the mixture stirred at 0° C. for a further 30 min. More sodium hydride (74 mg of a 60% dispersion in oil, 1.9 mmol) followed by iodomethane (0.12 mL, 1.9 mmol) were then added and the mixture stirred for 20 min at 0° C. followed by 30 min at room temperature. The solvent was evaporated and the residue partitioned between EtOAc (2×50 mL) and water (50 mL). The combined organic layers were dried (Na$_2$SO$_4$) and evaporated. The residue was chromatographed on silica gel, eluting with EtOAc:hexane (1:1) to afford the methyl ether (1.46 g, 93%) as a colourless oil. $^1$H NMR (360 MHz, d$_6$-DMSO) δ1.36 (9H, s), 2.26–2.37 (4H, m), 3.19 (3H, s), 3.24–3.33 (4H, m), 3.59–3.71 (3H, m), 7.13 (2H, dd, J$_{HA-HB}$=8.9 Hz and J$_{HA-F}$=8.9 Hz), 7.33 (2H, dd, J$_{HB-HA}$=8.9 Hz and J$_{HB-F}$=5.7 Hz). MS (ES$^+$) (339, M+1).

Step 4

1-[1-(4-Fluorophenyl)-2-methoxyethyl]piperazine

To a solution of 4-(tert-butyloxycarbonyl)-1-[1-(4-fluorophenyl)-2-methoxyethyl]piperazine (1.46 g, 4.3 mmol) in CH$_2$Cl$_2$ (40 mL) was added trifluoroacetic acid (4 mL), and the mixture stirred at room temperature for 3 h. The solvent was evaporated and the residue azeotroped with toluene (2×20 mL). The residue was partitioned between EtOAc (2×50 mL) and Na$_2$CO$_3$ solution (sat., 50 mL). The combined organic phases were dried (Na$_2$SO$_4$) and evaporated. The residue was chromatographed on silica gel, eluting with CH$_2$Cl$_2$:MeOH:NH$_3$ (90:10:1), to afford the piperazine (0.95 g, 92%) as a pale yellow oil. $^1$H NMR (360 MHz, CDCl$_3$) δ2.37–2.55 (4H, m), 2.86–2.89 (4H, m), 3.29 (3H, s), 3.45–3.48 (1H, m), 3.61 (1H, dd, J=9.9 and 5.2 Hz), 3.71 (1H, dd, J=9.9 and 5.8 Hz), 7.00 (2H, dd, J$_{HA-HB}$=8.7 Hz and J$_{HA-F}$=8.7 Hz), 7.27 (2H, dd, J$_{HB-HA}$=8.7 Hz and J$_{HB-F}$=5.6 Hz). MS (ES$^+$) (239, M+1).

Step 5

1-[3-(5-(1,2,4-Triazol-4-yl)-1H-indol-3-yl)propyl]-4-[1-(4-fluorophenyl)-2-methoxyethyl]piperazine. 1.4 Hydrogen Oxalate To a solution of Intermediate 3 (125 mg, 0.52 mmol) in THF (80 mL) was added triethylamine (144 μL, 1.03 mmol) and methanesulphonyl chloride (80 μL, 1.03 mmol). After stirring at room temperature for 2 h more triethylamine (72 μL, 0.51 mmol) followed by methanesulphonyl chloride (40 μL, 0.51 mmol) were added and the mixture stirred for a further 1 h. After this time the mixture was filtered and the filtrate evaporated in vacuo. The crude mesylate was used in the subsequent reaction without further purification.

To a suspension of the crude mesylate (prepared above) in iso-propanol (20 mL) was added K$_2$CO$_3$ (214 mg, 1.55 mmol), sodium iodide (77 mg, 0.52 mmol) and a solution of 1-[1-(4-fluorophenyl)-2-methoxyethyl]piperazine (615 mg, 2.6 mmol) in iso-propanol (5 mL). The mixture was heated at reflux, in the dark, for 3 h. The solution was allowed to cool to room temperature and the precipitate removed by filtration. The filtrate was evaporated and the residue partitioned between CH$_2$Cl$_2$ (2×50 mL) and water (50 mL). The combined organic layers were dried (Na$_2$SO$_4$) and evaporated. The residue was chromatographed on silica gel, eluting with CH$_2$Cl$_2$:MeOH (9:1→4:1), to give the title indole (232 mg, 97%) as a pale yellow foam. The hydrogen oxalate salt was prepared. mp. 100° C. (dec.). C$_{26}$H$_{31}$N$_6$OF. 1.4 (C$_2$H$_2$O$_4$). 1.5(H$_2$O) requires: C, 56.19; H, 6.03; N, 13.65%. Found: C, 56.56; H, 6.35; N, 13.34%. $^1$H NMR (360 MHz, d$_6$-DMSO) δ1.91–2.03 (2H, m), 2.50–3.23 (15H, m), 3.58–3.62 (1H, m), 3.67–3.71 (2H, m), 7.16 (2H, dd, J$_{HA-HB}$=8.9 Hz and J$_{HA-F}$=8.9 Hz), 7.30–7.37 (4H, m), 7.49 (2H, d, J=8.5 Hz), 7.78 (1H, d, J=1.9 Hz), 9.00 (2H, s), 11.17 (1H, br s). MS (ES$^+$) (463, M+1).

EXAMPLE 9

1-[3-(5-(1,2,4-Triazol-4-yl)-1H-indol-3-yl)propyl]-4-[2-benzyloxy-1-(4-fluorophenyl)ethyl]piperazine. 1.5 Hydrogen Oxalate Step 1

1-[2-Benzyloxy-1-(4-fluorophenyl)ethyl]-4-(tert-butyloxycarbonyl)piperazine

In the same way as that described in Example 8, Step 3 using 2-[4-tert-butyloxycarbonylpiperazin-1-yl]-2-[4-fluorophenyl]ethan-1-ol (1.5 g, 4.6 mmol), sodium hydride (204 mg of a 60% dispersion in oil, 5.1 mmol) and benzyl bromide (0.61 mL, 5.1 mmol). After stirring at room temperature for 30 min more sodium hydride (37 mg of a 60% dispersion in oil, 0.92 mmol) followed by benzyl bromide (0.11 mL, 0.92 mmol) was added. The residue was chromatographed on silica gel, eluting with EtOAc:hexane (1:4→1:2), to afford the benzyl ether (1.58 g, 82%) as a colourless oil. $^1$H NMR (250 MHz, CDCl$_3$) δ1.43 (9H, s), 2.30–2.55 (4H, m), 3.33–3.45 (4H, m), 3.51–3.60 (1H, m), 3.61–3.71 (1H, m), 3.73–3.85 (1H, m), 4.48 (2H, s), 6.96–7.04 (2H, m), 7.20–7.40 (7H, m). MS (ES$^+$) (415, M+1).

Step 2

1-[2-Benzyloxy-1-(4-fluorophenyl)ethyl]piperazine

In the same way as that described in Example 8, Step 4 using 1-[2-benzyloxy-1-(4-fluorophenyl)ethyl]-4-(tert-butyloxycarbonyl)piperazine (1.58 g, 3.8 mmol), trifluoroacetic acid (5 mL) and CH$_2$Cl$_2$ (50 mL). The piperazine (1.11 g, 92%) was isolated as a colourless oil. $^1$H NMR (250 MHz, CDCl$_3$) δ2.36–2.57 (4H, m), 2.84–2.89 (4H, m), 3.49–3.54 (1H, m), 3.65 (1H, dd, J=9.9 and 5.4 Hz), 3.79 (1H, dd, J=9.9 and 5.8 Hz), 4.47 (2H, s), 6.99 (1H, dd, J$_{HA-HB}$=8.7 Hz and J$_{HA-F}$=8.7 Hz), 7.20–7.35 (7H, m). MS (ES$^+$) (315, M+1).

Step 3

1-[3-(5-(1,2,4-Triazol-4-yl)-1H-indol-3-yl)propyl]-4-[2-benzyloxy-1-(4-fluorophenyl)ethyl]piperazine. 1.5 Hydrogen Oxalate In the same way as that described in Example 8, Step 5, using Intermediate 3 (100 mg, 0.41 mmol), triethylamine (172 μL, 1.24 mmol), methanesulphonyl chloride (96 μL, 1.24 mmol) and THF (70 mL). After stirring at room temperature for 3 h more triethylamine (57 μL, 0.41 mmol) followed by methanesulphonyl chloride (32 μL, 0.41 mmol) were added. After stirring at room temperature for a further 90 min the resultant crude mesylate was obtained and used crude in the subsequent reaction.

The crude mesylate (prepared above), 1-[2-benzyloxy-1-(4-fluorophenyl)ethyl]piperazine (649 mg, 2.07 mmol), K$_2$CO$_3$ (171 mg, 1.24 mmol), sodium iodide (62 mg) and iso-propanol (20 mL) were converted to the title compound in the same way as that described in Example 8, Step 5. The crude residue was chromatographed on silica gel, eluting with CH$_2$Cl$_2$:MeOH (92.5:7.5→85:15), to afford the piperazine (136 mg, 61%) as a pale yellow foam. The hydrogen oxalate salt was prepared. mp. 65° C. (dec.). C$_{32}$H$_{35}$N$_6$OF. 1.5(C$_2$H$_2$O$_4$). 0.3(H$_2$O) requires: C, 61.90; H, 5.73; N, 12.38%. Found: C, 61.90; H, 5.89; N, 12.46%. $^1$H NMR (360 MHz, d$_6$-DMSO+TFA) δ2.00–2.08 (2H, m), 2.50–3.76 (12H, m), 3.89–3.97 (1H, m), 4.02–4.11 (1H, m), 4.57–4.65 (3H, m), 7.27–7.46 (9H, m), 7.51–7.61 (3H, m), 7.95 (1H, s), 9.81 (2H, s), 11.33 (1H, br s). MS (ES$^+$) (539, M+1).

EXAMPLE 10

1-[3-(5-(1,2,4-Triazol-4-yl)-1H-indol-3-yl)propyl]-4-[2-(imidazol-1-yl)-1-phenylethyl]piperazine. 2.5 Hydrogen Oxalate Intermediate 4

1-(3-[5-(1,2,4-Triazol-4-yl)-1H-indol-3-yl]propyl)-4-[2-hydroxy-1-phenylethyl]piperazine a) Methyl 2-phenyl-2-[1-(3-(5-(1,2,4-triazol-4-yl)-1H-indol-3-yl)propyl)piperazin-4-yl]ethyl acetate In the same way as that described in Example 1, Step 2, using Intermediate 2 (200 mg, 0.64 mmol), methyl α-bromophenyl acetate (112 μL, 0.71 mmol), K$_2$CO$_3$ (98 mg, 0.71 mmol) and DMF (5 mL). The crude residue was chromatographed on silica gel, eluting with CH$_2$Cl$_2$:MeOH (93:7), to afford the ester (205 mg, 70%) as a cream foam. $^1$H NMR (250 MHz, CDCl$_3$) δ1.92–2.02 (2H, m), 2.42–2.70 (10H, m), 2.78 (2H, t, J=7.4 Hz), 3.67 (3H, s), 4.00 (1H, s), 7.10–7.18 (2H, m), 7.27–7.41 (5H, m), 7.48 (1H, d, J=8.5 Hz), 7.54 (1H, d, J=2.0 Hz), 8.47 (2H, s), 9.05 (1H, br s).

b) 1-(3-[5-(1,2,4-Triazol-4-yl)-1H-indol-3-yl]propyl)-4-[2-hydroxy-1-phenylethyl]piperazine In the same way as that described in Example 5, Step 3, using methyl 2-phenyl-2-[1-(3-(5-(1,2,4-triazol-4-yl)-1H-indol-3-yl)propyl)piperazin-4-yl]ethyl acetate (620 mg, 1.35 mmol), LiAlH$_4$ (1.62 mL of a 1.0M solution in ether, 1.62 mmol), THF (20 mL) and Na$_2$SO$_4$ solution (sat., 5 mL). The alcohol (485 mg, 84%) was isolated as a colourless foam. $^1$H NMR (360 MHz, CDCl$_3$) δ1.81–1.90 (2H, m), 2.32–2.70 (10H, m), 2.74 (2H, t, J=7.6 Hz), 3.64–3.70 (2H, m), 3.96 (1H, t, J=11 Hz), 7.11–7.19 (4H, m), 7.28–7.35 (3H, m), 7.45 (1H, d, J=8.6 Hz), 7.52 (1H, d, J=2.0 Hz), 8.35 (1H, br s), 8.44 (2H, s). MS (431, M+1).

1-[3-(5-(1,2,4-Triazol-4-yl)-1H-indol-3-yl)propyl]-4-[2-(imidazol-1-yl)-1-phenylethyl]piperazine. 2.5 Hydrogen Oxalate In the same way as that described in Example 6, using 1-(3-[5-(1,2,4-triazol-4-yl)-1H-indol-3-yl]propyl)-4-[2-hydroxy-1-phenylethyl]piperazine (100 mg, 0.23 mmol), triethylamine (65 μL, 0.47 mmol), methanesulphonyl chloride (36 μL, 0.47 mmol) and THF (5 mL). The crude mesylate was then reacted with imidazole (317 mg, 4.7 mmol) in the same way as that described in Example 6. The title compound (13 mg, 12%) was isolated as a pale yellow gum. The hydrogen oxalate salt was prepared. mp. 130° C. (dec.). C$_{28}$H$_{32}$N$_8$. 2.5(C$_2$H$_2$O$_4$). 1.2(H$_2$O) requires: C, 54.50; H, 5.46; N, 15.41%. Found: C, 54.36; H, 5.48; N, 15.59%. $^1$H NMR (250 MHz, d$_6$-DMSO) δ1.95–2.12 (2H, m), 2.45–3.50 (14H, m), 5.65–5.70 (1H, m), 7.12 (1H, s), 7.33–7.51 (9H, m), 7.79 (1H, d, J=1.9 Hz), 8.27 (1H, s), 9.02 (2H, s), 11.19 (1H, br s). MS (ES$^+$) (481, M+1).

EXAMPLE 11

1-[3-(5-(1,2,4-Triazol-4-yl)-1H-indol-3-yl)propyl]-4-[1-phenyl-2-(pyrrolidin-1-yl)ethyl]piperazine. 2.4 Hydrogen Oxalate In the same way as that described in Example 6, using 1-[3-(5-(1,2,4-triazol-4-yl)-1H-indol-3-yl)propyl]-4-[2-hydroxy-1-phenylethyl]piperazine (167 mg, 0.39 mmol), triethylamine (108 μL, 0.78 mmol), methanesulphonyl chloride (60 μL, 0.78 mmol) and THF (8 mL). The crude mesylate was then reacted with pyrrolidine (0.65 mL, 7.8 mmol) in the same way as that described in Example 6. The title amine (39 mg, 21%) was isolated as pale yellow foam. The hydrogen oxalate salt was prepared. mp. 135° C. (dec.). C$_{29}$H$_{37}$N$_7$. 2.4(C$_2$H$_2$O$_4$). H$_2$O requires: C, 56.56; H, 6.15; N, 13.66%. Found: C, 56.65; H, 6.35; N, 13.37%. $^1$H NMR (360 MHz, d$_6$-DMSO) δ1.66–1.86 (4H, m), 1.97–2.07 (2H, m), 2.43–3.33 (18H, m), 4.43–4.51 (1H, m), 7.29–7.34 (2H, m), 7.42–7.52 (6H, m), 7.79 (1H, s), 9.01 (2H, s), 11.17 (1H, br s). MS (ES$^+$) (484, M+1).

EXAMPLE 12

1-[3-(5-(1,2,4-Triazol-4-yl)-1H-indol-3-yl)propyl]-4-[2-(oxazolidin-2-on-3-yl)-1-phenylethyl]piperazine. 1.25 Hydrogen Oxalate Step 1

1-[3-(5-(1,2,4-Triazol-4-yl)-1H-indol-3-yl)propyl]-4-[2-amino-1-phenylethyl]piperazine In the same way as that described in Example 7, Step 1 using 1-[3-(5-(1,2,4-triazol-4-yl)-1H-indol-3-yl)propyl]-4-[2-hydroxy-1-phenylethyl]piperazine (330 mg, 0.77 mmol), triethylamine (214 μL, 1.53 mmol), methanesulphonyl chloride (118 μL, 1.53 mmol) and THF (15 mL). The crude mesylate was then reacted with ammonia (7.7 mL of a 2.0M solution in MeOH, 15.3 mmol) in the same way as that described in Example 7, Step 1. The amine (185 mg, 56%) was isolated as a pale yellow foam. $^1$H NMR (250 MHz, CDCl$_3$) δ1.88–2.00 (2H, m), 2.38–2.76 (12H, m), 2.79 (2H, t, J=7.5 Hz), 4.11 (1H, dd, J=10.4 and 3.6 Hz), 7.13–7.18 (2H, m), 7.22–7.39 (5H, m), 7.47 (1H, d, J=8.6 Hz), 7.59 (1H, s), 8.34 (1H, br s), 8.46 (2H, s). MS (430, M+1).

Step 2

1-[3-(5-(1,2,4-Triazol-4-yl)-1H-indol-3-yl)propyl]-4-[2-(2-(2-chloroethylcarbamoyl)-1-phenylethyl]piperazine In the same way as that described in Example 7, Step 2, using 1-[3-(5-(1,2,4-triazol-4-yl)-1H-indol-3-yl)propyl]-4-[2-amino-1-phenylethyl]piperazine (138 mg, 0.32 mmol), 2-chloroethyl chloroformate (35 μL, 0.34 mmol), NaOH solution (142 μL of a 10% (w/v) solution, 0.35 mmol), dioxane (3 mL) and water (1.5 mL). The carbamate (106 mg, 62%) was isolated as a colourless foam. $^1$H NMR (360 MHz, CDCl$_3$) δ1.88–1.99 (2H, m), 2.37–2.68 (12H, m), 2.77–2.83 (2H, m), 3.50–3.77 (2H, m), 4.20–4.33 (2H, m), 4.61–4.71 (1H, m), 5.77–5.85 (1H, m), 7.13–7.16 (2H, m), 7.21–7.35 (5H, m), 7.46 (1H, d, J=8.5 Hz), 7.56 (1H, d, J=2.0 Hz), 8.37 (1H, br s), 8.46 (2H, s). MS(ES$^+$) (536/538, M+1).

Step 3

1-[3-(5-(1,2,4-Triazol-4-yl)-1H-indol-3-yl)propyl]-4-[2-(oxazolidin-2-on-3-yl)-1-phenylethyl]piperazine. 1.25 Hydrogen Oxalate In the same way as that described in Example 7, Step 3, using 1-[3-(5-(1,2,4-triazol-4-yl)-1H-indol-3-yl)propyl]-4-[2-(2-chloroethylcarbamoyl)-1-phenylethyl]piperazine (106 mg, 0.2 mmol), sodium hydride (10 mg of a 60% dispersion in mineral oil, 0.25 mmol) and DMF (4 mL). The crude residue was chromatographed on silica gel, eluting with CH$_2$Cl$_2$:MeOH:NH$_3$ (95:5:0.5). The title compound (87 mg, 87%) was isolated as a colourless foam. The hydrogen oxalate salt was prepared. mp. 136° C. (dec.). C$_{28}$H$_{33}$N$_7$O$_2$. 1.25(C$_2$H$_2$O$_4$). 0.25(H$_2$O) requires: C, 59.41; H, 5.88; N, 15.90%. Found: C, 59.32; H, 5.96; N, 15.78%. $^1$H NMR (360 MHz, d$_6$-DMSO) δ1.95–2.07 (2H, m), 2.49–3.14 (14H, m), 3.26–3.34 (1H, m), 3.56–3.65 (1H, m), 4.20–4.33 (2H, m), 4.98–5.05 (1H, m), 7.30–7.41 (7H, m), 7.49 (1H, d, J=8.5 Hz), 7.80 (1H, d, J=2.0 Hz), 9.01 (2H, s), 11.16 (1H, br s). MS (ES$^+$) (500, M+1).

EXAMPLE 13

1-[3-(5-(1,2,4-Triazol-4-yl)-1H-indol-3-yl)propyl]-4-[2-(oxazol-2-on-3-yl)-1-phenylethyl]piperazine. 1.5 Hydrogen Oxalate To a solution of 1-[3-(5-(1,2,4-triazol-4-yl)-1H-indol-3-yl)propyl]-4-[2-hydroxy-1-phenylethyl]piperazine (100 mg, 0.23 mmol) in THF (5 mL) at 0° C., was added triethylamine (49 μL, 0.35 mmol) followed by methanesulphonyl chloride (27 μL, 0.35 mmol). The cooling bath was removed and the mixture stirred at room temperature for 35 min. The solid was removed by filtration and the filtrate partially evaporated (approx. 3 mL remaining) and diluted with DMF (5 mL). This filtrate was then added to a solution of oxazol-2-one sodium salt in DMF (2 mL). (The sodium salt was prepared by adding sodium hydride (18.6 mg of a 60% dispersion in mineral oil, 0.47 mmol) to a solution of oxazol-2-one (40 mg, 0.47 mmol) in DMF (2 mL) and stirring for 1 h at room temperature). The mixture was stirred at room temperature for 90 min then the solvent was removed in vacuo and the residue partitioned between CH$_2$Cl$_2$ (2×25 mL) and water (20 mL). The combined organic layers were dried (Na$_2$SO$_4$) and evaporated. The residue was chromatographed on silica gel, eluting with CH$_2$Cl$_2$:MeOH:NH$_3$ (90:10:0→90:10:1). The title compound (30 mg, 26%) was isolated as a cream foam. The hydrogen oxalate salt was prepared, mp. 125° C. (dec.). C$_{28}$H$_{31}$N$_7$O$_2$. 1.5(C$_2$H$_2$O$_4$). 0.5(H$_2$O) requires: C, 58.03; H, 5.50; N, 15.28%. Found: C, 58.23; H, 5.73; N, 15.38%. $^1$H NMR (360 MHz, d$_6$-DMSO) δ1.93–2.07 (2H, m), 2.47–3.30 (14H, m), 5.15–5.21 (1H, m), 7.21 (1H, d, J=2.0 Hz), 7.27–7.40 (8H, m), 7.49 (1H, d, J=8.6 Hz), 7.79 (1H, d, J=1.9 Hz), 9.01 (2H, s), 11.16 (1H, br s). MS (ES$^+$) (498, M+1).

EXAMPLE 14

1-[3-(5-(1,2,4-Triazol-4-yl)-1H-indol-3-yl)propyl]-4-[3-(imidazol-1-yl)-1-phenylpropyl]piperazine. 2.5 Hydrogen Oxalate In the same way as that described in Example 6, using 1-[3-(5-(1,2,4-triazol-4-yl)-1H-indol-3-yl)propyl]-4-[3-hydroxy-1-phenylpropyl]piperazine (200 mg, 0.45 mmol), triethylamine (125 μL, 0.9 mmol), methanesulphonyl chloride (70 μL, 0.9 mmol) and THF (10 mL). The crude mesylate was then reacted with imidazole (613 mg, 9.0 mmol) in the same way as that described in Example 6, to give the title compound (57 mg, 26%) as a pale yellow foam. The hydrogen oxalate salt was prepared. mp. 90° C. (dec.). C$_{29}$H$_{34}$N$_8$. 2.5(C$_2$H$_2$O$_4$). 2.5(H$_2$O) requires: C, 53.40; H, 5.80; N, 14.65%. Found: C, 53.34; H, 5.86; N, 14.50%. $^1$H NMR (360 MHz, d$_6$-DMSO) δ1.98–2.09 (2H, m), 2.26–2.43 (4H, m), 2.57–2.81 (6H, m), 2.98–3.21 (6H, m), 5.46–5.55 (1H, m), 7.11 (1H, s), 7.27–7.42 (7H, m), 7.46 (1H, s), 7.51 (1H, d, J=8.6Hz), 7.81 (1H, s), 8.20 (1H, s), 9.02 (2H, s), 11.18 (1H, br s). MS (ES$^+$) (495, M+1).

We claim:

1. A compound of formula I, or a salt thereof:

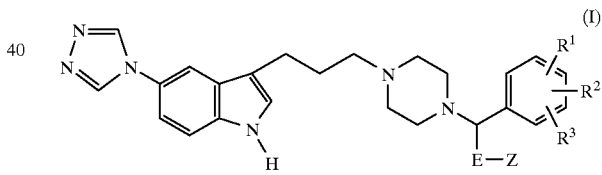

wherein

R$^1$ represents hydrogen, halogen, trifluoromethyl, C$_{1-6}$ alkoxy or a group of formula (a):

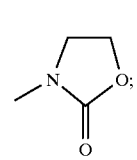

R$^2$ and R$^3$ independently represent hydrogen, halogen, trifluoromethyl or C$_{1-6}$ alkoxy;

E represents a straight or branched alkylene chain containing from 1 to 4 carbon atoms; and Z represents hydroxy, C$_{1-6}$ alkoxy, aryl(C$_{1-6}$)alkoxy, an imidazolyl or pyrrolidinyl group, or a group of formula (Za) or (Zb):

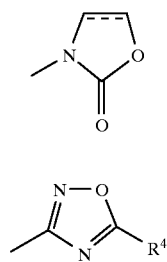

in which the broken line represents an optional chemical bond; and

R⁴ represents $C_{1-6}$ alkyl.

2. A compound as claimed in claim 1 represented by formula II, and salts thereof:

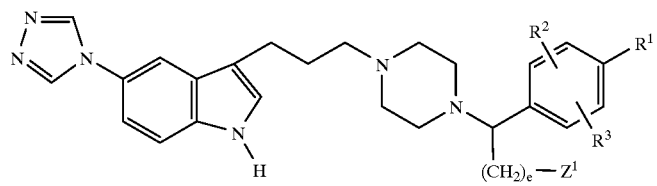

wherein $R^1$, $R^2$ and $R^3$ are as defined in claim 1;

e is 1 or 2; and $Z^1$ represents hydroxy, methoxy, benzyloxy, imidazol-1-yl, pyrrolidin-1-yl, oxazol-2-on-3-yl, oxazolidin-2-on-3-yl or 5-methyl-1,2,4-oxadiazol-3-yl.

3. A compound as claimed in claim 2 wherein $R^1$ represents hydrogen, fluoro or trifluoromethyl.

4. A compound as claimed in claim 2 wherein $R^2$ is hydrogen and $R^3$ is other than hydrogen.

5. A compound as claimed in claim 2 wherein $R^2$ and $R^3$ are both hydrogen.

6. A compound as claimed in claim 3 wherein $R^2$ is hydrogen and $R^3$ is other than hydrogen.

7. A compound as claimed in claim 3 wherein $R^2$ and $R^3$ are both hydrogen.

8. A compound selected from:

1-[3-(5-(1,2,4-triazol-4-yl)-1H-indol-3-yl)propyl]-4-[2-(oxazol-2-on-3-yl)-1-phenylethyl]piperazine;
1-[3-(5-(1,2,4-triazol-4-yl)-1H-indol-3-yl)propyl]-4-[2-(oxazolidin-2-on-3-yl)-1-phenylethyl]piperazine;
1-[3-(5-(1,2,4-triazol-4-yl)-1H-indol-3-yl)propyl]-4-[1-(4-fluorophenyl)-2-(oxazolidin-2-on-3-yl)ethyl]piperazine;
1-[3-(5-(1,2,4-triazol-4-yl)-1H-indol-3-yl)propyl]-4-(3-hydroxy-1-phenylpropyl)piperazine;
1-[3-(5-(1,2,4-triazol-4-yl)-1H-indol-3-yl)propyl]-4-[2-(imidazol-1-yl)-1-phenylethyl]piperazine;
1-[3-(5-(1,2,4-triazol-4-yl)-1H-indol-3-yl)propyl]-4-[1-(4-fluorophenyl)-2-hydroxyethyl]piperazine;
1-[3-(5-(1,2,4-triazol-4-yl)-1H-indol-3-yl)propyl]-4-[1-(4-fluorophenyl)-2-methoxyethyl]piperazine;
1-[3-(5-(1,2,4-triazol-4-yl)-1H-indol-3-yl)propyl]-4-[3-(5-methyl-1,2,4-oxadiazol-3-yl)-1-phenylpropyl]piperazine;
1-[3-(5-(1,2,4-triazol-4-yl)-1H-indol-3-yl)propyl]-4-[2-benzyloxy-1-(4-fluorophenyl)ethyl]piperazine;
1-[3-(5-(1,2,4-triazol-4-yl)-1H-indol-3-yl)propyl]-4-[1-(4-fluorophenyl)-3-methoxypropyl]piperazine;
1-[3-(5-(1,2,4-triazol-4-yl)-1H-indol-3-yl)propyl]-4-[1-(4-fluorophenyl)-2-(imidazol-1-yl)ethyl]piperazine;
1-[3-(5-(1,2,4-triazol-4-yl)-1H-indol-3-yl)propyl]-4-[1-phenyl-2-(pyrrolidin-1-yl)ethyl]piperazine;
1-[3-(5-(1,2,4-triazol-4-yl)-1H-indol-3-yl)propyl]-4-[1-(4-fluorophenyl)-3-hydroxypropyl]piperazine;
1-[3-(5-(1,2,4-triazol-4-yl)-1H-indol-3-yl)propyl]-4-[3-(imidazol-1-yl)-1-phenylpropyl]piperazine;

and salts thereof.

9. A pharmaceutical composition comprising a compound of formula I as defined in claim 1 or a pharmaceutically acceptable salt thereof thereof in association with a pharmaceutically acceptable carrier.

10. A process for the preparation of a compound as claimed in any one of claims 1 to 6, which comprises:

(A) reacting the compound of formula III with a compound of formula IV:

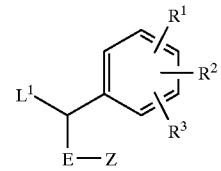

wherein $R^1$, $R^2$, $R^3$, E and Z are as defined in claim 1, and $L^1$ represents a suitable leaving group; or (B) reacting the compound of formula III as defined above with a compound of formula V:

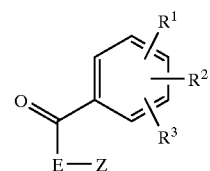

wherein $R^1$, $R^2$, $R^3$, E and Z are as defined in claim 1; in the presence of a reducing agent; or (C) reacting the compound of formula VI:

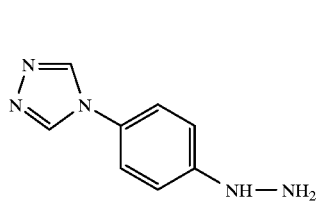
(VI)

with a compound of formula XI, or a carbonyl-protected form thereof:

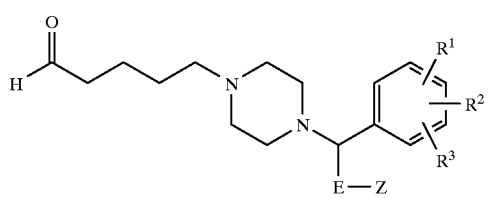
(XI)

wherein $R^1$, $R^2$, $R^3$, E and Z are as defined in claim 1; or (D) reacting a compound of formula XIII:

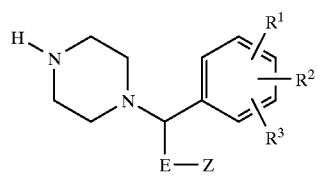
(XIII)

wherein $R^1$, $R^2$, $R^3$, E and Z are as defined in claim 1; with a compound of formula XIV:

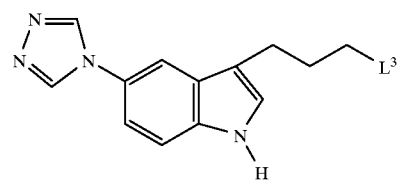
(XIV)

wherein $L^3$ represents a suitable leaving group; or (E) reducing a compound of formula XVII:

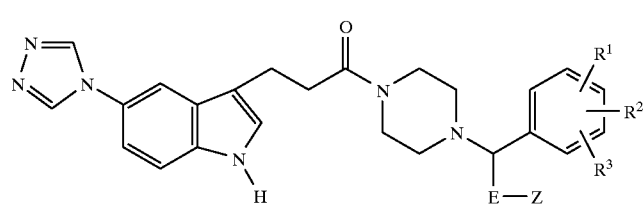
(XVII)

wherein $R^1$, $R^2$, $R^3$, E and Z are as defined in claim 1; or (F) reducing a compound of formula XIX:

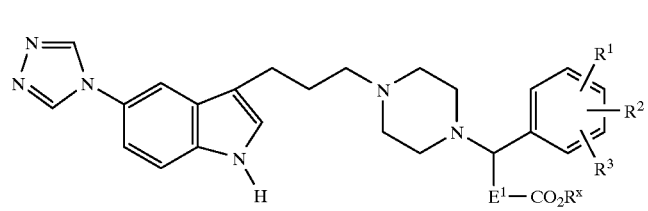
(XIX)

wherein $E^1$ represents a chemical bond or a straight or branched alkylene chain containing from 1 to 3 carbon atoms, $R^x$ represents $C_{1-6}$ alkyl, and $R^1$, $R^2$ and $R^3$ are as defined in claim 1; or (G) reacting a compound of formula XX with a compound of formula XXI:

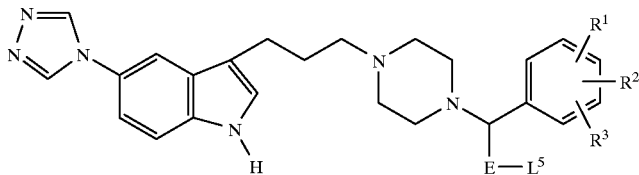 

(XX) (XXI)

wherein $Z^2$ represents imidazol-1-yl, pyrrolidin-1-yl, oxazol-2-on-3-yl or oxazolidin-2-on-3-yl, $L^5$ represents a suitable leaving group, and $R^1$, $R^2$, $R^3$ and E are as defined in claim 1.

11. A method for the treatment and/or prevention of migraine, cluster headache, chronic paroxysmal hemicrania, headache associated with vascular disorders, tension headache or paediatric migraine, which method comprises administering to a patient in need of such treatment an effective amount of a compound of formula I as defined in claim 1 or a pharmaceutically acceptable salt thereof.

* * * * *